United States Patent
Romer et al.

(10) Patent No.: US 11,827,678 B2
(45) Date of Patent: *Nov. 28, 2023

(54) ARTICLES COMPRISING A SILK POLYPEPTIDE FOR ANTIGEN DELIVERY

(71) Applicants: AMSILK GmbH, Planegg/Martinsried (DE); Ludwig-Maximilians-Universitat Munchen, Munich (DE); Universitat Bayreuth, Bayreuth (DE)

(72) Inventors: Lin Romer, Munich (DE); Ute Slotta, Munich (DE); Julia Engert, Munich (DE); Gerhard Winter, Penzberg (DE); Matthias Lucke, Munich (DE); Thomas Scheibel, Bayreuth (DE)

(73) Assignees: Amsilk GmbH, Munich (DE); Ludwig-Maximilians-Universitat Munchen, Munich (DE); Universitat Bayreuth, Bayreuth (DE)

( * ) Notice: Subject to any disclaimer, the term of this patent is extended or adjusted under 35 U.S.C. 154(b) by 119 days.

This patent is subject to a terminal disclaimer.

(21) Appl. No.: 17/383,926

(22) Filed: Jul. 23, 2021

(65) Prior Publication Data

US 2021/0347832 A1   Nov. 11, 2021

Related U.S. Application Data

(62) Division of application No. 16/307,622, filed as application No. PCT/EP2017/064436 on Jun. 13, 2017, now Pat. No. 11,104,708.

(30) Foreign Application Priority Data

Jun. 22, 2016 (EP) .................................. 16175724

(51) Int. Cl.
| | |
|---|---|
| A61K 39/00 | (2006.01) |
| C07K 14/435 | (2006.01) |
| A61K 39/385 | (2006.01) |
| A61K 47/64 | (2017.01) |
| A61K 47/65 | (2017.01) |
| A61P 35/00 | (2006.01) |
| A61K 47/42 | (2017.01) |
| C12N 15/62 | (2006.01) |
| A61K 38/00 | (2006.01) |

(52) U.S. Cl.
CPC ...... *C07K 14/43518* (2013.01); *A61K 39/385* (2013.01); *A61K 47/42* (2013.01); *A61K 47/646* (2017.08); *A61K 47/65* (2017.08); *A61P 35/00* (2018.01); *C07K 14/43586* (2013.01); *C12N 15/62* (2013.01); *A61K 38/00* (2013.01); *A61K 2039/6031* (2013.01); *A61K 2039/627* (2013.01); *C07K 2319/40* (2013.01); *C07K 2319/50* (2013.01)

(58) Field of Classification Search
CPC ................................................ C07K 14/43518
See application file for complete search history.

(56) References Cited

U.S. PATENT DOCUMENTS

| | | | |
|---|---|---|---|
| 11,104,708 B2* | 8/2021 | Romer | ................... A61K 47/65 |
| 2004/0096987 A1 | 5/2004 | Geacintov | |
| 2005/0124540 A1 | 6/2005 | Hovanessian | |
| 2008/0171059 A1 | 7/2008 | Howland | |

FOREIGN PATENT DOCUMENTS

| | | |
|---|---|---|
| EP | 1391509 A1 | 2/2004 |
| JP | 2013-521801 A | 6/2013 |
| WO | 93/24836 A1 | 12/1993 |
| WO | 2008/022774 A2 | 2/2008 |
| WO | 2011/071368 A1 | 6/2011 |
| WO | 2011069643 A2 | 6/2011 |
| WO | 2011115538 A1 | 9/2011 |
| WO | 2013142901 A1 | 10/2013 |

OTHER PUBLICATIONS

International Search Report in PCT/EP2017/064436, dated Aug. 29, 2017.
Gomes, et al.. "Antimicrobial functionalized genetically engineered spider silk." Biomaterials 32, No. 18 (2011): 4255-4266.
Müller, et al. "Silicatein expression in the hexactinellid Crateromorpha meyeri: the lead marker gene restricted to siliceous sponges." Cell and tissue research 333, No. 2 (May 31, 2008): 339-351.
Thatikonda, et al. "Genetic fusion of single-chain variable fragments to partial spider silk improves target detection in micro-and nanoarrays." Biotechnology journal 11, No. 3 (2016): 437-448.

* cited by examiner

*Primary Examiner* — Albert M Navarro
(74) *Attorney, Agent, or Firm* — Kilpatrick Townsend & Stockton LLP

(57) ABSTRACT

The present invention relates to a polypeptide comprising a silk polypeptide and an antigen. Further, the present invention relates to an article comprising the polypeptide. Furthermore, the present invention relates to a pharmaceutical composition comprising the article. In addition, the present invention relates to the article or pharmaceutical composition for use as a pharmaceutical, for inducing an immune response and/or for use in a prophylactic and/or therapeutic treatment of a disease.

17 Claims, 10 Drawing Sheets
Specification includes a Sequence Listing.

SEQUENCE LISTING

```
<160> NUMBER OF SEQ ID NOS: 23

<210> SEQ ID NO 1
<211> LENGTH: 7
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(7)
<223> OTHER INFORMATION: Cathepsin S cleavable linker
```

```
<400> SEQUENCE: 1

Gly Pro Met Gly Leu Pro Gly
1               5

<210> SEQ ID NO 2
<211> LENGTH: 9
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(9)
<223> OTHER INFORMATION: Cathepsin S amd B cleavable linker

<400> SEQUENCE: 2

Gly Ala Val Gly Phe Leu Gly Ile Gly
1               5

<210> SEQ ID NO 3
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module C (ADF-4)

<400> SEQUENCE: 3

Gly Ser Ser Ala Ala Ala Ala Ala Ala Ala Ser Gly Pro Gly Gly
1               5                   10                  15

Tyr Gly Pro Glu Asn Gln Gly Pro Ser Gly Pro Gly Gly Tyr Gly Pro
                20                  25                  30

Gly Gly Pro
        35

<210> SEQ ID NO 4
<211> LENGTH: 35
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(35)
<223> OTHER INFORMATION: Module Cc

<400> SEQUENCE: 4

Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Gly Tyr Gly Pro
                20                  25                  30

Gly Gly Pro
        35

<210> SEQ ID NO 5
<211> LENGTH: 14
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(14)
<223> OTHER INFORMATION: T7-Tag
```

```
<400> SEQUENCE: 5

Gly Cys Gly Gly Ser Gly Gly Gly Ser Gly Gly Gly Gly
1               5                   10

<210> SEQ ID NO 6
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: DOMAIN
<222> LOCATION: (1)..(8)
<223> OTHER INFORMATION: T7-Tag

<400> SEQUENCE: 6

Gly Gly Cys Gly Gly Ser Gly Gly
1               5

<210> SEQ ID NO 7
<211> LENGTH: 124
<212> TYPE: PRT
<213> ORGANISM: Artificial Sequence
<220> FEATURE:
<223> OTHER INFORMATION: based on ADF-3
<220> FEATURE:
<221> NAME/KEY: DOMAIN
<222> LOCATION: (1)..(124)
<223> OTHER INFORMATION: NR3 (ADF-3)

<400> SEQUENCE: 7

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
            20                  25                  30

Ala Ala Ser Ser Arg Val Ser Ser Ala Val Ser Ser Leu Val Ser Ser
        35                  40                  45

Gly Pro Thr Asn Gln Ala Ala Leu Ser Asn Thr Ile Ser Ser Val Val
    50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95

Ser Ser Ser Ile Gly Gln Ile Asn Tyr Gly Ala Ser Ala Gln Tyr Thr
            100                 105                 110

Gln Met Val Gly Gln Ser Val Ala Gln Ala Leu Ala
        115                 120

<210> SEQ ID NO 8
<211> LENGTH: 109
<212> TYPE: PRT
<213> ORGANISM: Artificial Sequence
<220> FEATURE:
<223> OTHER INFORMATION: based on ADF-4
<220> FEATURE:
<221> NAME/KEY: DOMAIN
<222> LOCATION: (1)..(109)
<223> OTHER INFORMATION: NR4 (ADF-4)

<400> SEQUENCE: 8

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
```

```
            20                  25                  30

Ser Leu Val Ser Ser Gly Pro Thr Asn Gly Ala Ala Val Ser Gly Ala
        35                  40                  45

Leu Asn Ser Leu Val Ser Gln Ile Ser Ala Ser Asn Pro Gly Leu Ser
    50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95

Val Ser Gln Ser Thr Gln Met Ile Ser Gln Ala Leu Ser
            100                 105

<210> SEQ ID NO 9
<211> LENGTH: 136
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(136)
<223> OTHER INFORMATION: derived from Latrodectus hesperus (NR5)

<400> SEQUENCE: 9

Met Gly Gln Ala Asn Thr Pro Trp Ser Ser Lys Ala Asn Ala Asp Ala
1               5                   10                  15

Phe Ile Asn Ser Phe Ile Ser Ala Ala Ser Asn Thr Gly Ser Phe Ser
            20                  25                  30

Gln Asp Gln Met Glu Asp Met Ser Leu Ile Gly Asn Thr Leu Met Ala
        35                  40                  45

Ala Met Asp Asn Met Gly Gly Arg Ile Thr Pro Ser Lys Leu Gln Ala
    50                  55                  60

Leu Asp Met Ala Phe Ala Ser Ser Val Ala Glu Ile Ala Ala Ser Glu
65                  70                  75                  80

Gly Gly Asp Leu Gly Val Thr Thr Asn Ala Ile Ala Asp Ala Leu Thr
                85                  90                  95

Ser Ala Phe Tyr Gln Thr Thr Gly Val Val Asn Ser Arg Phe Ile Ser
            100                 105                 110

Glu Ile Arg Ser Leu Ile Gly Met Phe Ala Gln Ala Ser Ala Asn Asp
        115                 120                 125

Val Tyr Ala Ser Ala Gly Ser Gly
    130                 135

<210> SEQ ID NO 10
<211> LENGTH: 137
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(137)
<223> OTHER INFORMATION: derived from Latrodectus hesperus (NR6)

<400> SEQUENCE: 10

Met Gly Gln Ala Asn Thr Pro Trp Ser Ser Lys Glu Asn Ala Asp Ala
1               5                   10                  15

Phe Ile Gly Ala Phe Met Asn Ala Ala Ser Gln Ser Gly Ala Phe Ser
            20                  25                  30

Ser Asp Gln Ile Asp Asp Met Ser Val Ile Ser Asn Thr Leu Met Ala
```

```
                35                  40                  45
Ala Met Asp Asn Met Gly Gly Arg Ile Thr Gln Ser Lys Leu Gln Ala
 50                  55                  60

Leu Asp Met Ala Phe Ala Ser Ser Val Ala Glu Ile Ala Val Ala Asp
 65                  70                  75                  80

Gly Gln Asn Val Gly Ala Ala Thr Asn Ala Ile Ser Asp Ala Leu Arg
                 85                  90                  95

Ser Ala Phe Tyr Gln Thr Thr Gly Val Val Asn Asn Gln Phe Ile Thr
                100                 105                 110

Gly Ile Ser Ser Leu Ile Gly Met Phe Ala Gln Val Ser Gly Asn Glu
            115                 120                 125

Val Ser Tyr Ser Ser Ala Gly Ser Gly
130                 135

<210> SEQ ID NO 11
<211> LENGTH: 8
<212> TYPE: PRT
<213> ORGANISM: artificial
<220> FEATURE:
<223> OTHER INFORMATION: synthetic
<220> FEATURE:
<221> NAME/KEY: domain
<222> LOCATION: (1)..(8)
<223> OTHER INFORMATION: epitope of chicken-Ovalbumin

<400> SEQUENCE: 11

Ser Ile Ile Asn Phe Glu Lys Leu
1               5

<210> SEQ ID NO 12
<211> LENGTH: 576
<212> TYPE: PRT
<213> ORGANISM: artificial
<220> FEATURE:
<223> OTHER INFORMATION: synthetic
<220> FEATURE:
<221> NAME/KEY: REPEAT
<222> LOCATION: (1)..(576)
<223> OTHER INFORMATION: C16

<400> SEQUENCE: 12

Met Ala Ser Met Thr Gly Gly Gln Gln Met Gly Arg Gly Ser Met Gly
1               5                   10                  15

Ser Ser Ala Ala Ala Ala Ala Ala Ala Ser Gly Pro Gly Gly Tyr
                20                  25                  30

Gly Pro Glu Asn Gln Gly Pro Ser Gly Pro Gly Gly Tyr Gly Pro Gly
            35                  40                  45

Gly Pro Gly Ser Ser Ala Ala Ala Ala Ala Ala Ala Ala Ser Gly Pro
 50                  55                  60

Gly Gly Tyr Gly Pro Glu Asn Gln Gly Pro Ser Gly Pro Gly Gly Tyr
 65                  70                  75                  80

Gly Pro Gly Gly Pro Gly Ser Ser Ala Ala Ala Ala Ala Ala Ala Ala
                 85                  90                  95

Ser Gly Pro Gly Gly Tyr Gly Pro Glu Asn Gln Gly Pro Ser Gly Pro
                100                 105                 110

Gly Gly Tyr Gly Pro Gly Gly Pro Gly Ser Ser Ala Ala Ala Ala Ala
            115                 120                 125

Ala Ala Ala Ser Gly Pro Gly Gly Tyr Gly Pro Glu Asn Gln Gly Pro
130                 135                 140

Ser Gly Pro Gly Gly Tyr Gly Pro Gly Gly Pro Gly Ser Ser Ala Ala
```

```
            145                 150                 155                 160
        Ala Ala Ala Ala Ala Ala Ser Gly Pro Gly Gly Tyr Gly Pro Glu Asn
                        165                 170                 175
        Gln Gly Pro Ser Gly Pro Gly Gly Tyr Gly Pro Gly Gly Pro Gly Ser
                        180                 185                 190
        Ser Ala Ala Ala Ala Ala Ala Ala Ser Gly Pro Gly Gly Tyr Gly
                    195                 200                 205
        Pro Glu Asn Gln Gly Pro Ser Gly Pro Gly Gly Tyr Gly Pro Gly Gly
                210                 215                 220
        Pro Gly Ser Ser Ala Ala Ala Ala Ala Ala Ser Gly Pro Gly
        225                 230                 235                 240
        Gly Tyr Gly Pro Glu Asn Gln Gly Pro Ser Gly Pro Gly Gly Tyr Gly
                        245                 250                 255
        Pro Gly Gly Pro Gly Ser Ser Ala Ala Ala Ala Ala Ala Ala Ser
                    260                 265                 270
        Gly Pro Gly Gly Tyr Gly Pro Glu Asn Gln Gly Pro Ser Gly Pro Gly
                    275                 280                 285
        Gly Tyr Gly Pro Gly Gly Pro Gly Ser Ser Ala Ala Ala Ala Ala
                290                 295                 300
        Ala Ala Ser Gly Pro Gly Gly Tyr Gly Pro Glu Asn Gln Gly Pro Ser
        305                 310                 315                 320
        Gly Pro Gly Gly Tyr Gly Pro Gly Gly Pro Gly Ser Ser Ala Ala Ala
                        325                 330                 335
        Ala Ala Ala Ala Ala Ser Gly Pro Gly Gly Tyr Gly Pro Glu Asn Gln
                    340                 345                 350
        Gly Pro Ser Gly Pro Gly Gly Tyr Gly Pro Gly Gly Pro Gly Ser Ser
                    355                 360                 365
        Ala Ala Ala Ala Ala Ala Ala Ser Gly Pro Gly Gly Tyr Gly Pro
                370                 375                 380
        Glu Asn Gln Gly Pro Ser Gly Pro Gly Gly Tyr Gly Pro Gly Gly Pro
        385                 390                 395                 400
        Gly Ser Ser Ala Ala Ala Ala Ala Ala Ala Ser Gly Pro Gly Gly
                        405                 410                 415
        Tyr Gly Pro Glu Asn Gln Gly Pro Ser Gly Pro Gly Gly Tyr Gly Pro
                    420                 425                 430
        Gly Gly Pro Gly Ser Ser Ala Ala Ala Ala Ala Ala Ser Gly
                    435                 440                 445
        Pro Gly Gly Tyr Gly Pro Glu Asn Gln Gly Pro Ser Gly Pro Gly Gly
                    450                 455                 460
        Tyr Gly Pro Gly Gly Pro Gly Ser Ser Ala Ala Ala Ala Ala Ala
        465                 470                 475                 480
        Ala Ser Gly Pro Gly Gly Tyr Gly Pro Glu Asn Gln Gly Pro Ser Gly
                        485                 490                 495
        Pro Gly Gly Tyr Gly Pro Gly Gly Pro Gly Ser Ser Ala Ala Ala Ala
                    500                 505                 510
        Ala Ala Ala Ala Ser Gly Pro Gly Gly Tyr Gly Pro Glu Asn Gln Gly
                    515                 520                 525
        Pro Ser Gly Pro Gly Gly Tyr Gly Pro Gly Gly Pro Gly Ser Ser Ala
                    530                 535                 540
        Ala Ala Ala Ala Ala Ala Ser Gly Pro Gly Gly Tyr Gly Pro Glu
        545                 550                 555                 560
        Asn Gln Gly Pro Ser Gly Pro Gly Gly Tyr Gly Pro Gly Gly Pro Gly
                        565                 570                 575
```

<210> SEQ ID NO 13
<211> LENGTH: 588
<212> TYPE: PRT
<213> ORGANISM: artificial
<220> FEATURE:
<223> OTHER INFORMATION: synthetic
<220> FEATURE:
<221> NAME/KEY: REPEAT
<222> LOCATION: (1)..(585)
<223> OTHER INFORMATION: C16-SIINFEKL

<400> SEQUENCE: 13

Met Ala Ser Met Thr Gly Gly Gln Gln Met Gly Arg Gly Ser Met Gly
1               5                   10                  15

Ser Ser Ala Ala Ala Ala Ala Ala Ala Ser Gly Pro Gly Gly Tyr
            20                  25                  30

Gly Pro Glu Asn Gln Gly Pro Ser Gly Pro Gly Gly Tyr Gly Pro Gly
            35                  40                  45

Gly Pro Gly Ser Ser Ala Ala Ala Ala Ala Ala Ser Gly Pro
50                  55                  60

Gly Gly Tyr Gly Pro Glu Asn Gln Gly Pro Ser Gly Pro Gly Gly Tyr
65                  70                  75                  80

Gly Pro Gly Gly Pro Gly Ser Ser Ala Ala Ala Ala Ala Ala
                85                  90                  95

Ser Gly Pro Gly Gly Tyr Gly Pro Glu Asn Gln Gly Pro Ser Gly Pro
            100                 105                 110

Gly Gly Tyr Gly Pro Gly Gly Pro Gly Ser Ser Ala Ala Ala Ala
            115                 120                 125

Ala Ala Ala Ser Gly Pro Gly Gly Tyr Gly Pro Glu Asn Gln Gly Pro
            130                 135                 140

Ser Gly Pro Gly Gly Tyr Gly Pro Gly Gly Pro Gly Ser Ser Ala Ala
145                 150                 155                 160

Ala Ala Ala Ala Ala Ser Gly Pro Gly Gly Tyr Gly Pro Glu Asn
                165                 170                 175

Gln Gly Pro Ser Gly Pro Gly Gly Tyr Gly Pro Gly Gly Pro Gly Ser
            180                 185                 190

Ser Ala Ala Ala Ala Ala Ala Ser Gly Pro Gly Gly Tyr Gly
            195                 200                 205

Pro Glu Asn Gln Gly Pro Ser Gly Pro Gly Gly Tyr Gly Pro Gly Gly
            210                 215                 220

Pro Gly Ser Ser Ala Ala Ala Ala Ala Ala Ala Ser Gly Pro Gly
225                 230                 235                 240

Gly Tyr Gly Pro Glu Asn Gln Gly Pro Ser Gly Pro Gly Gly Tyr Gly
                245                 250                 255

Pro Gly Gly Pro Gly Ser Ser Ala Ala Ala Ala Ala Ala Ala Ser
            260                 265                 270

Gly Pro Gly Gly Tyr Gly Pro Glu Asn Gln Gly Pro Ser Gly Pro Gly
            275                 280                 285

Gly Tyr Gly Pro Gly Gly Pro Gly Ser Ser Ala Ala Ala Ala Ala
            290                 295                 300

Ala Ala Ser Gly Pro Gly Gly Tyr Gly Pro Glu Asn Gln Gly Pro Ser
305                 310                 315                 320

Gly Pro Gly Gly Tyr Gly Pro Gly Gly Pro Gly Ser Ser Ala Ala Ala
                325                 330                 335

Ala Ala Ala Ala Ala Ser Gly Pro Gly Gly Tyr Gly Pro Glu Asn Gln

```
                 340                 345                 350
Gly Pro Ser Gly Pro Gly Gly Tyr Gly Pro Gly Gly Pro Ser Ser
                355                 360                 365
Ala Ala Ala Ala Ala Ala Ala Ser Gly Pro Gly Gly Tyr Gly Pro
            370                 375                 380
Glu Asn Gln Gly Pro Ser Gly Pro Gly Gly Tyr Gly Pro Gly Gly
385                 390                 395                 400
Gly Ser Ser Ala Ala Ala Ala Ala Ala Ala Ser Gly Pro Gly Gly
                405                 410                 415
Tyr Gly Pro Glu Asn Gln Gly Pro Ser Gly Pro Gly Gly Tyr Gly Pro
                420                 425                 430
Gly Gly Pro Gly Ser Ser Ala Ala Ala Ala Ala Ala Ala Ser Gly
                435                 440                 445
Pro Gly Gly Tyr Gly Pro Glu Asn Gln Gly Pro Ser Gly Pro Gly Gly
                450                 455                 460
Tyr Gly Pro Gly Gly Pro Gly Ser Ser Ala Ala Ala Ala Ala Ala
465                 470                 475                 480
Ala Ser Gly Pro Gly Gly Tyr Gly Pro Glu Asn Gln Gly Pro Ser Gly
                485                 490                 495
Pro Gly Gly Tyr Gly Pro Gly Gly Pro Gly Ser Ser Ala Ala Ala
                500                 505                 510
Ala Ala Ala Ala Ser Gly Pro Gly Gly Tyr Gly Pro Glu Asn Gln Gly
                515                 520                 525
Pro Ser Gly Pro Gly Gly Tyr Gly Pro Gly Gly Pro Gly Ser Ser Ala
                530                 535                 540
Ala Ala Ala Ala Ala Ala Ser Gly Pro Gly Gly Tyr Gly Pro Glu
545                 550                 555                 560
Asn Gln Gly Pro Ser Gly Pro Gly Gly Tyr Gly Pro Gly Gly Pro Gly
                565                 570                 575
Gly Ser Gly Ser Ile Ile Asn Phe Glu Lys Leu Gly
                580                 585

<210> SEQ ID NO 14
<211> LENGTH: 591
<212> TYPE: PRT
<213> ORGANISM: artificial
<220> FEATURE:
<223> OTHER INFORMATION: synthetic
<220> FEATURE:
<221> NAME/KEY: REPEAT
<222> LOCATION: (1)..(591)
<223> OTHER INFORMATION: eADF4(C16-CathS-CD8)

<400> SEQUENCE: 14

Met Ala Ser Met Thr Gly Gly Gln Gln Met Gly Arg Gly Ser Met Gly
1               5                   10                  15
Ser Ser Ala Ala Ala Ala Ala Ala Ala Ser Gly Pro Gly Gly Tyr
                20                  25                  30
Gly Pro Glu Asn Gln Gly Pro Ser Gly Pro Gly Gly Tyr Gly Pro Gly
                35                  40                  45
Gly Pro Gly Ser Ser Ala Ala Ala Ala Ala Ala Ala Ser Gly Pro
                50                  55                  60
Gly Gly Tyr Gly Pro Glu Asn Gln Gly Pro Ser Gly Pro Gly Gly Tyr
65                  70                  75                  80
Gly Pro Gly Gly Pro Gly Ser Ser Ala Ala Ala Ala Ala Ala Ala
                85                  90                  95
```

-continued

Ser Gly Pro Gly Gly Tyr Gly Pro Glu Asn Gln Gly Pro Ser Gly Pro
          100                 105                 110

Gly Gly Tyr Gly Pro Gly Gly Pro Gly Ser Ser Ala Ala Ala Ala Ala
          115                 120                 125

Ala Ala Ala Ser Gly Pro Gly Gly Tyr Gly Pro Glu Asn Gln Gly Pro
130                 135                 140

Ser Gly Pro Gly Gly Tyr Gly Pro Gly Gly Pro Gly Ser Ser Ala Ala
145                 150                 155                 160

Ala Ala Ala Ala Ala Ala Ser Gly Pro Gly Gly Tyr Gly Pro Glu Asn
                165                 170                 175

Gln Gly Pro Ser Gly Pro Gly Gly Tyr Gly Pro Gly Gly Pro Gly Ser
              180                 185                 190

Ser Ala Ala Ala Ala Ala Ala Ala Ser Gly Pro Gly Gly Tyr Gly
          195                 200                 205

Pro Glu Asn Gln Gly Pro Ser Gly Pro Gly Gly Tyr Gly Pro Gly Gly
          210                 215                 220

Pro Gly Ser Ser Ala Ala Ala Ala Ala Ala Ala Ser Gly Pro Gly
225                 230                 235                 240

Gly Tyr Gly Pro Glu Asn Gln Gly Pro Ser Gly Pro Gly Gly Tyr Gly
                245                 250                 255

Pro Gly Gly Pro Gly Ser Ser Ala Ala Ala Ala Ala Ala Ala Ser
              260                 265                 270

Gly Pro Gly Gly Tyr Gly Pro Glu Asn Gln Gly Pro Ser Gly Pro Gly
          275                 280                 285

Gly Tyr Gly Pro Gly Gly Pro Gly Ser Ser Ala Ala Ala Ala Ala Ala
          290                 295                 300

Ala Ala Ser Gly Pro Gly Gly Tyr Gly Pro Glu Asn Gln Gly Pro Ser
305                 310                 315                 320

Gly Pro Gly Gly Tyr Gly Pro Gly Gly Pro Gly Ser Ser Ala Ala Ala
                325                 330                 335

Ala Ala Ala Ala Ala Ser Gly Pro Gly Gly Tyr Gly Pro Glu Asn Gln
          340                 345                 350

Gly Pro Ser Gly Pro Gly Gly Tyr Gly Pro Gly Gly Pro Gly Ser Ser
          355                 360                 365

Ala Ala Ala Ala Ala Ala Ala Ser Gly Pro Gly Gly Tyr Gly Pro
          370                 375                 380

Glu Asn Gln Gly Pro Ser Gly Pro Gly Gly Tyr Gly Pro Gly Gly Pro
385                 390                 395                 400

Gly Ser Ser Ala Ala Ala Ala Ala Ala Ala Ser Gly Pro Gly Gly
                405                 410                 415

Tyr Gly Pro Glu Asn Gln Gly Pro Ser Gly Pro Gly Gly Tyr Gly Pro
              420                 425                 430

Gly Gly Pro Gly Ser Ser Ala Ala Ala Ala Ala Ala Ala Ser Gly
          435                 440                 445

Pro Gly Gly Tyr Gly Pro Glu Asn Gln Gly Pro Ser Gly Pro Gly Gly
          450                 455                 460

Tyr Gly Pro Gly Gly Pro Gly Ser Ser Ala Ala Ala Ala Ala Ala
465                 470                 475                 480

Ala Ser Gly Pro Gly Gly Tyr Gly Pro Glu Asn Gln Gly Pro Ser Gly
                485                 490                 495

Pro Gly Gly Tyr Gly Pro Gly Gly Pro Gly Ser Ser Ala Ala Ala Ala
              500                 505                 510

Ala Ala Ala Ala Ser Gly Pro Gly Gly Tyr Gly Pro Glu Asn Gln Gly

-continued

```
            515                 520                 525
Pro Ser Gly Pro Gly Gly Tyr Gly Pro Gly Gly Pro Gly Ser Ser Ala
            530                 535                 540

Ala Ala Ala Ala Ala Ala Ser Gly Pro Gly Gly Tyr Gly Pro Glu
545                 550                 555                 560

Asn Gln Gly Pro Ser Gly Pro Gly Gly Tyr Gly Pro Gly Gly Pro Gly
            565                 570                 575

Pro Met Gly Leu Pro Gly Ser Ile Ile Asn Phe Glu Lys Leu Gly
            580                 585                 590

<210> SEQ ID NO 15
<211> LENGTH: 593
<212> TYPE: PRT
<213> ORGANISM: artificial
<220> FEATURE:
<223> OTHER INFORMATION: synthetic
<220> FEATURE:
<221> NAME/KEY: REPEAT
<222> LOCATION: (1)..(593)
<223> OTHER INFORMATION: eADF4(C16-CathB-CD8)

<400> SEQUENCE: 15

Met Ala Ser Met Thr Gly Gly Gln Gln Met Gly Arg Gly Ser Met Gly
1               5                   10                  15

Ser Ser Ala Ala Ala Ala Ala Ala Ala Ser Gly Pro Gly Gly Tyr
            20                  25                  30

Gly Pro Glu Asn Gln Gly Pro Ser Gly Pro Gly Gly Tyr Gly Pro Gly
            35                  40                  45

Gly Pro Gly Ser Ser Ala Ala Ala Ala Ala Ala Ala Ser Gly Pro
50                  55                  60

Gly Gly Tyr Gly Pro Glu Asn Gln Gly Pro Ser Gly Pro Gly Gly Tyr
65                  70                  75                  80

Gly Pro Gly Gly Pro Gly Ser Ser Ala Ala Ala Ala Ala Ala Ala
            85                  90                  95

Ser Gly Pro Gly Gly Tyr Gly Pro Glu Asn Gln Gly Pro Ser Gly Pro
            100                 105                 110

Gly Gly Tyr Gly Pro Gly Gly Pro Gly Ser Ser Ala Ala Ala Ala
            115                 120                 125

Ala Ala Ala Ser Gly Pro Gly Gly Tyr Gly Pro Glu Asn Gln Gly Pro
            130                 135                 140

Ser Gly Pro Gly Gly Tyr Gly Pro Gly Gly Pro Gly Ser Ser Ala Ala
145                 150                 155                 160

Ala Ala Ala Ala Ala Ser Gly Pro Gly Gly Tyr Gly Pro Glu Asn
            165                 170                 175

Gln Gly Pro Ser Gly Pro Gly Gly Tyr Gly Pro Gly Gly Pro Gly Ser
            180                 185                 190

Ser Ala Ala Ala Ala Ala Ala Ser Gly Pro Gly Gly Tyr Gly
            195                 200                 205

Pro Glu Asn Gln Gly Pro Ser Gly Pro Gly Gly Tyr Gly Pro Gly Gly
            210                 215                 220

Pro Gly Ser Ser Ala Ala Ala Ala Ala Ala Ala Ser Gly Pro Gly
225                 230                 235                 240

Gly Tyr Gly Pro Glu Asn Gln Gly Pro Ser Gly Pro Gly Gly Tyr Gly
            245                 250                 255

Pro Gly Gly Pro Gly Ser Ser Ala Ala Ala Ala Ala Ala Ala Ser
            260                 265                 270
```

-continued

Gly Pro Gly Gly Tyr Gly Pro Glu Asn Gln Gly Pro Ser Gly Pro Gly
            275                 280                 285

Gly Tyr Gly Pro Gly Gly Pro Gly Ser Ser Ala Ala Ala Ala Ala Ala
        290                 295                 300

Ala Ala Ser Gly Pro Gly Gly Tyr Gly Pro Glu Asn Gln Gly Pro Ser
305                 310                 315                 320

Gly Pro Gly Gly Tyr Gly Pro Gly Gly Pro Gly Ser Ser Ala Ala Ala
                325                 330                 335

Ala Ala Ala Ala Ser Gly Pro Gly Gly Tyr Gly Pro Glu Asn Gln
            340                 345                 350

Gly Pro Ser Gly Pro Gly Gly Tyr Gly Pro Gly Gly Pro Gly Ser Ser
            355                 360                 365

Ala Ala Ala Ala Ala Ala Ala Ser Gly Pro Gly Gly Tyr Gly Pro
    370                 375                 380

Glu Asn Gln Gly Pro Ser Gly Pro Gly Gly Tyr Gly Pro Gly Gly Pro
385                 390                 395                 400

Gly Ser Ser Ala Ala Ala Ala Ala Ala Ser Gly Pro Gly Gly
            405                 410                 415

Tyr Gly Pro Glu Asn Gln Gly Pro Ser Gly Pro Gly Gly Tyr Gly Pro
        420                 425                 430

Gly Gly Pro Gly Ser Ser Ala Ala Ala Ala Ala Ala Ala Ser Gly
            435                 440                 445

Pro Gly Gly Tyr Gly Pro Glu Asn Gln Gly Pro Ser Gly Pro Gly Gly
            450                 455                 460

Tyr Gly Pro Gly Gly Pro Gly Ser Ser Ala Ala Ala Ala Ala Ala
465                 470                 475                 480

Ala Ser Gly Pro Gly Gly Tyr Gly Pro Glu Asn Gln Gly Pro Ser Gly
            485                 490                 495

Pro Gly Gly Tyr Gly Pro Gly Gly Pro Gly Ser Ser Ala Ala Ala
            500                 505                 510

Ala Ala Ala Ala Ser Gly Pro Gly Gly Tyr Gly Pro Glu Asn Gln Gly
            515                 520                 525

Pro Ser Gly Pro Gly Gly Tyr Gly Pro Gly Gly Pro Gly Ser Ser Ala
            530                 535                 540

Ala Ala Ala Ala Ala Ala Ser Gly Pro Gly Gly Tyr Gly Pro Glu
545                 550                 555                 560

Asn Gln Gly Pro Ser Gly Pro Gly Gly Tyr Gly Pro Gly Gly Pro Gly
                565                 570                 575

Ala Val Gly Phe Leu Gly Ile Gly Ser Ile Ile Asn Phe Glu Lys Leu
            580                 585                 590

Gly

<210> SEQ ID NO 16
<211> LENGTH: 11
<212> TYPE: PRT
<213> ORGANISM: artificial
<220> FEATURE:
<223> OTHER INFORMATION: synthetic
<220> FEATURE:
<221> NAME/KEY: DOMAIN
<222> LOCATION: (1)..(11)
<223> OTHER INFORMATION: sequence cleaved from the hybrid polypeptide
      comprising the cathepsin B cleavable linker and the epitope of
      chicken-Ovalbumin (OVA257-264)

<400> SEQUENCE: 16

Ile Gly Ser Ile Ile Asn Phe Glu Lys Leu Gly

<210> SEQ ID NO 17
<211> LENGTH: 12
<212> TYPE: PRT
<213> ORGANISM: artificial
<220> FEATURE:
<223> OTHER INFORMATION: synthetic
<220> FEATURE:
<221> NAME/KEY: DOMAIN
<222> LOCATION: (1)..(12)
<223> OTHER INFORMATION: sequence cleaved from the hybrid polypeptide
      comprising the cathepsin S cleavable linker and the epitope of
      chicken-Ovalbumin (OVA257-264)

<400> SEQUENCE: 17

Leu Pro Gly Ser Ile Ile Asn Phe Glu Lys Leu Gly
1               5                   10

<210> SEQ ID NO 18
<211> LENGTH: 35
<212> TYPE: PRT
<213> ORGANISM: artificial
<220> FEATURE:
<223> OTHER INFORMATION: synthetic
<220> FEATURE:
<221> NAME/KEY: DOMAIN
<222> LOCATION: (1)..(35)
<223> OTHER INFORMATION: C kappa

<400> SEQUENCE: 18

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Gly Tyr Gly Pro
                20                  25                  30

Gly Gly Pro
        35

<210> SEQ ID NO 19
<211> LENGTH: 11
<212> TYPE: PRT
<213> ORGANISM: artificial
<220> FEATURE:
<223> OTHER INFORMATION: syntetic
<220> FEATURE:
<221> NAME/KEY: DOMAIN
<222> LOCATION: (1)..(11)
<223> OTHER INFORMATION: T7-Tag

<400> SEQUENCE: 19

Met Ala Ser Met Thr Gly Gly Gln Gln Met Gly
1               5                   10

<210> SEQ ID NO 20
<211> LENGTH: 5
<212> TYPE: PRT
<213> ORGANISM: artificial
<220> FEATURE:
<223> OTHER INFORMATION: Cathepsin S cleavage site
<220> FEATURE:
<221> NAME/KEY: domain
<222> LOCATION: (1)..(5)

<400> SEQUENCE: 20

Pro Met Gly Leu Pro
1               5

<210> SEQ ID NO 21

```
<211> LENGTH: 4
<212> TYPE: PRT
<213> ORGANISM: artificial
<220> FEATURE:
<223> OTHER INFORMATION: Cathepsin B cleavage site
<220> FEATURE:
<221> NAME/KEY: domain
<222> LOCATION: (1)..(4)

<400> SEQUENCE: 21

Gly Phe Leu Gly
1

<210> SEQ ID NO 22
<211> LENGTH: 4
<212> TYPE: PRT
<213> ORGANISM: artificial
<220> FEATURE:
<223> OTHER INFORMATION: Cathepsin B cleavage site
<220> FEATURE:
<221> NAME/KEY: domain
<222> LOCATION: (1)..(4)

<400> SEQUENCE: 22

Ala Leu Ala Leu
1

<210> SEQ ID NO 23
<211> LENGTH: 4
<212> TYPE: PRT
<213> ORGANISM: artificial
<220> FEATURE:
<223> OTHER INFORMATION: Cathepsin B cleavage site
<220> FEATURE:
<221> NAME/KEY: domain
<222> LOCATION: (1)..(4)

<400> SEQUENCE: 23

Gly Gly Gly Phe
1
```

ARTICLES COMPRISING A SILK POLYPEPTIDE FOR ANTIGEN DELIVERY

CROSS REFERENCE TO RELATED APPLICATIONS

This application is a divisional of U.S. application Ser. No. 16/307,622, filed Dec. 6, 2018, which is a 371 National Stage Application of PCT/EP2017/064436, International Filing Date Jun. 13, 2017, which claims priority to EP 16175724.0 filed Jun. 22, 2016, the disclosures of which are incorporated herein by reference for all purposes.

REFERENCE TO SUBMISSION OF A SEQUENCE LISTING AS A TEXT FILE

The Sequence Listing written in file Sequence Listing 1116752.txt created on Dec. 5, 2018, 32,768 bytes, machine format IBM-PC, MS-Windows operating system, is hereby incorporated by reference in its entirety for all purposes.

The present invention relates to a polypeptide comprising a silk polypeptide and an antigen. Further, the present invention relates to an article comprising the polypeptide. Furthermore, the present invention relates to a pharmaceutical composition comprising the article. In addition, the present invention relates to the article or pharmaceutical composition for use as a pharmaceutical, for inducing an immune response and/or for use in a prophylactic and/or therapeutic treatment of a disease.

BACKGROUND OF THE INVENTION

Antigen delivery into animal cells, e.g. human cells, is important in the medical field. It has, for example, high potential in the commercial area of vaccination. It is, in addition, highly relevant with respect to the improvement of therapeutic approaches for treating animals, e.g. humans. Cancer, autoimmune diseases, mycosis, infections with viruses and bacteria or therapeutic vaccination against Hepatitis B/C or HIV are, for example, promising targets for immunotherapeutic treatments.

Immunization by vaccination is one of the most productive tools in modern medical practice. The body's ability to protect itself from foreign pathogens relies on its ability to recognize and react to infectious materials once they are presented to the host immune cells, in a process known as the adaptive immune response. Currently employed compositions for immunization deliver antigens with a mixture of stabilizers, preservatives, and adjuvants. The antigen is typically a protein component of a bacterium or virus. The vaccine comprising the antigen induces both humoral and cellular responses to said antigen. The effectiveness of such vaccination largely depends on the antigen's immunogenicity, which is in turn a function of the antigen's size, molecular complexity, degree of "foreignness" and capacity to be cleaved into peptides by antigen-presenting cells (APCs). The antigen-stimulated and activated APCs migrate to draining lymph nodes (DLNs), where the antigen is then presented to naïve T helper cells. Subsequently the antigen is presented to B cells resulting in systemic antibody production as well as priming of memory B cells. The initial production of antibodies begins to decline approximately three weeks post-primary exposure, but can be further enhanced via a second contact with the same antigen. Therefore, booster shots are strongly advocated and generally induce high concentrations of antigen-specific antibodies. Dendritic cells (DCs) as specialized antigen-presenting cells (APCs) play critical roles in both innate and adaptive immunity. DCs are specialized antigen-presenting cells with the unique capability to capture and process antigens, migrate from the periphery to a lymphoid organ, and present the antigens to resting T cells in a major histocompatibility complex (MHC)-restricted fashion.

However, one of the drawbacks of the currently available antigen delivery material is the cytotoxic effect this material has on target cells. Given the potential therapeutic and clinical uses of the delivery material, less cytotoxic material is needed to carry antigens into various cells without affecting inherent signaling pathways and systems. In addition, vaccines comprising antigens are often not sufficiently absorbed by the cells/internalized into the cells. Thus, there is a need for a non-cytotoxic article comprising an antigen having a structure which is preferentially absorbed by the cells/internalized into the cells. Moreover, artificial antigen carrier vehicle which are composed of a single chain polypeptide comprising a carrier polypeptide and an antigen are not known in the art.

The inventors of the present patent application produced for the first time antigen carrier articles which are composed of a single chain polypeptide comprising a silk polypeptide as carrier polypeptide as well as an antigen. Further, the inventors of the present patent application surprisingly found that antigens which are part of articles, e.g. particles, comprising silk polypeptides are preferentially taken up by animal cells, e.g. human cells. In this context, the inventors of the present patent application were surprised that the articles, e.g. particles, which are mainly composed of silk, function as an auxiliary material which stabilizes the antigen and makes it transportable. The articles, e.g. particles, can be degraded within the organism (e.g. human body) without traces. Furthermore, the inventors of the present patent application surprisingly found that the use of adjuvants in a pharmaceutical composition comprising antigens which are part of the articles, e.g. particles, comprising silk polypeptides is no longer required. The effectiveness of an antigen comprised in a composition without adjuvants is at least as good as or comparable to the same antigen comprised in a composition with adjuvants. The omission of adjuvants has the positive effect that side effects and vaccine incompatibility can be reduced, in some cases even avoided. In addition, the articles, e.g. particles, comprising silk polypeptides and antigens are non-toxic, in particular non-cytotoxic, and non-immunogenic. The articles, e.g. particles, can be readily manufactured in an one-step production process without the need of organic solvents or toxic substances. Additionally, a one-step production process reduces the risks of harmful impurities or contaminations and has significant advantages regarding documentation and regulatory aspects. A one-step production process means that no additional loading step is necessary after article formation. The one-step production process is particularly desirable as it is easily up-scalable to manufacturing scale. Furthermore the antigen is exactly defined by the genetic code in the polypeptide and can, therefore, not be degraded in the course of the otherwise needed loading procedure.

SUMMARY OF THE INVENTION

In a first aspect, the present invention relates to a polypeptide comprising
(i) a silk polypeptide and
(ii) an antigen.

In a second aspect, the present invention relates to a nucleic acid molecule encoding the polypeptide of the first aspect.

In a third aspect, the present invention relates to a method for producing a polypeptide comprising the step of:
(a) expressing the nucleic acid molecule of the second aspect in a cell, thereby producing the polypeptide in the cell.

In a fourth aspect, the present invention relates to an article comprising the polypeptide of the first aspect.

In a fifth aspect, the present invention relates to a method for producing an article comprising the steps of:
(a) providing an aqueous solution comprising the polypeptide of the first aspect, and
(b) forming an article out of/from the solution provided in (a).

In a sixth aspect, the present invention relates to a pharmaceutical composition comprising the article of the fourth aspect.

In a seventh aspect, the present invention relates to the article of the fourth aspect or the pharmaceutical composition of sixth aspect for use as a pharmaceutical.

In an eight aspect, the present invention relates to the article of the fourth aspect or the pharmaceutical composition of sixth aspect for inducing an immune response.

In a ninth aspect, the present invention relates to the article of the fourth aspect or the pharmaceutical composition of sixth aspect for use in a prophylactic and/or therapeutic treatment of a disease.

In a tenth aspect, the present invention relates to a method for delivering an antigen to a cell comprising administering to a subject the article of the fourth aspect or the pharmaceutical composition of the sixth aspect.

In an eleventh aspect, the present invention relates to a method for inducing an immune response in a subject comprising administering to a subject the article of the fourth aspect or the pharmaceutical composition of the sixth aspect.

In a twelfth aspect, the present invention relates to a method for prophylactic and/or therapeutic treatment of a disease in a subject comprising administering to a subject the article of the fourth aspect or the pharmaceutical composition of the sixth aspect.

In a thirteenth aspect, the present invention relates to a method for stimulating, priming, and/or expanding T cells in a subject comprising administering to a subject the article of the fourth aspect or the pharmaceutical composition of the sixth aspect.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The terms "polypeptide" and "protein" are used interchangeably in the context of the present invention. They refer to a long peptide-linked chain of amino acids, e.g. one that is typically 40 amino acids long or longer than 40 amino acids.

The term "peptide", as used herein, refers to a short peptide-linked chain of amino acids, e.g. one that is typically less than about 40 amino acids long and more typically less than about 30 amino acids long.

The terms "fusion protein" or "hybrid protein" (literally, made of parts from different sources) are used interchangeably in the context of the present invention. They refer to a protein which is created through the joining of two or more genes that originally coded for separate proteins/peptides. Translation of this fusion gene results in a single chain polypeptide with functional properties derived from each of the original proteins/peptides.

The terms "recombinant fusion protein" or "recombinant hybrid protein" are used interchangeably in the context of the present invention. They refer to a single chain polypeptide which is created artificially by recombinant DNA technology.

In one embodiment, the polypeptide of the present invention is a fusion or hybrid polypeptide comprising a silk polypeptide and an antigen. In one preferred embodiment, the polypeptide of the present invention is a fusion or hybrid polypeptide comprising a silk polypeptide, an antigen, and an enzymatically cleavable linker, wherein the antigen is attached to the silk polypeptide via the enzymatically cleavable linker or wherein the enzymatically cleavable linker is located between the silk polypeptide and the antigen. The sequence of the enzymatically cleavable linker may be modified by adding further non-functional amino acids.

The term "silk polypeptide", as used herein, refers to a polypeptide which shows, in comparison to other polypeptides, a quite aberrant amino acid composition. In particular, a silk polypeptide possess large quantities of hydrophobic amino acids such as glycine or alanine, but, for example, no (or only very little) tryptophan. In addition, a silk polypeptide contains highly repetitive amino acid sequences or repetitive units (repeat units, modules), especially in their large core domain.

Based on DNA analysis, it was shown that all silk polypeptides are chains of repetitive units which further comprise a limited set of distinct shorter peptide motifs. The expressions "peptide motif" and "consensus sequence" can be used interchangeably herein. Generally, the silk consensus sequences can be grouped into four major categories: GPGXX, GGX, $A_x$ or $(GA)_n$ and spacers. These categories of peptide motifs in silk polypeptides have been assigned structural roles. For example, it has been suggested that the GPGXX motif is involved in a β-turn spiral, probably providing elasticity. The GGX motif is known to be responsible for a glycine-rich $3_1$-helix. Both GPGXX and GGX motifs are thought to be involved in the formation of an amorphous matrix that connects crystalline regions, thereby providing elasticity of the fiber. Alanine-rich motifs typically contain 6-9 residues and have been found to form crystalline β-sheets. The spacers typically contain charged groups and separate the iterated peptide motifs into clusters. Preferably, the silk polypeptide is a spider silk polypeptide. More preferably, the silk polypeptide, e.g. spider silk polypeptide, is a recombinant polypeptide.

The term "antigen", as used herein, relates to an molecule comprising an epitope against which an immune response is to be generated. The term "antigen" includes proteins or peptides. The term "antigen" also includes molecules, which become antigenic only through transformation (e.g. intermediately in the molecule or by completion with body protein). An antigen is preferably presentable by cells of the immune system such as antigen presenting cells (APCs) like dendritic cells (DCs) or macrophages. In addition, an antigen or a processing product thereof is preferably recognizable by a T or B cell receptor, or by an immunoglobulin molecule such as an antibody. The antigen may be a disease-associated antigen, such as a tumor antigen, a viral antigen, or a bacterial antigen.

In the context of the present invention, the term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may, therefore, be used for therapeutic purposes. Disease-associated antigens are preferably associated with infection by microbes, typically microbial antigens, or associated with cancer, typically tumors.

The term "disease", as used herein, refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

As mentioned above, the disease may be an infectious disease or an autoimmune disease. The disease may also be a cancer disease or simply cancer.

The term "infectious disease", as used herein, refers to any disease which can be transmitted from individual to individual or from organism to organism, and is caused by a microbial agent (e.g. common cold). Infectious diseases are known in the art and include, for example, a viral disease, a bacterial disease, or a parasitic disease. Said diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The term "autoimmune disease", as used herein, refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The terms "cancer disease" or "cancer", as used herein, refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

As mentioned above, the antigen may be a tumor antigen, a viral antigen, or a bacterial antigen.

The term "tumor antigen", as used herein, refers to a constituent of cancer cells which may be derived from the cytoplasm, the cell surface, and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

The term "viral antigen", as used herein, refers to any viral component having antigenic properties, i.e. being able to provoke an immune response in an individual. The viral antigen may be a viral ribonucleoprotein or an envelope protein.

The term "microbial antigen", as used herein, refers to any microbial component having antigenic properties, i.e. being able to provoke an immune response in an individual.

The term "bacterial antigen", as used herein, refers to any bacterial component having antigenic properties, i.e. being able to provoke an immune response in an individual. The bacterial antigen may be derived from the cell wall or cytoplasm membrane of a bacterium.

The term "fungal antigen", as used herein, refers to any fungal component having antigenic properties, i.e. being able to provoke an immune response in an individual.

The term "zooparasitic antigen", as used herein, refers to any component of a parasite of an animal having antigenic properties, i.e. being able to provoke an immune response in an individual. Said parasite may be a flea, louse, or worm.

The term "immune response", as used herein, relates to a reaction of the immune system to immunogenic organisms, such as bacteria, viruses, cells or substances. The term "immune response" includes the innate immune response and the adaptive immune response. Preferably, the immune response is related to an activation of immune cells, an induction of cytokine biosynthesis, and/or antibody production. It is preferred that the immune response induced by the articles of the present invention (or more specifically by the antigens being part of it) comprises the steps of activation of antigen presenting cells (APCs), such as dendritic cells (DCs) and/or macrophages, presentation of the antigen or fragment thereof by said antigen presenting cells and activation of cytotoxic T cells due to this presentation.

The term "immune cells", as used herein, refers to cells of the immune system which are involved in defending the body of an individual. The term "immune cells" encompasses specific types of immune cells and their precursors including leucocytes comprising macrophages, monocytes (precursors of macrophages), granulocytes such as neutrophils, eosinophils and basophils, dendritic cells, mast cells, and lymphocytes such as B cells, T cells and natural killer (NK) cells. Macrophages, monocytes (precursors of macrophages), neutrophils, dendritic cells (DCs), and mast cells are phagocytic cells.

The term "antigen presenting cell (APC)", as used herein, is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells", as used herein, relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells (DCs) and macrophages.

The term "non-professional antigen presenting cells", as used herein, relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

The term "dendritic cell (DC)", as used herein, refers to another subtype of phagocytic cells belonging to the class of antigen presenting cells (APCs). Preferably, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. Preferably, the dendritic cells are splenic dendritic cells.

The term "macrophage", as used herein, refers to a subgroup of phagocytic cells produced by the differentiation of monocytes. Macrophages which are activated by inflammation, immune cytokines, or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells (APCs). Preferably, the macrophages are splenic macrophages.

The terms "T cells" or "T lymphocytes", as used herein, relate to types of lymphocytes that play a central role in cell-mediated immunity. T cells or T lymphocytes can be distinguished from other lymphocytes, such as B cells and natural killer (NK) cells, by the presence of a T cell receptor (TCR) on the cell surface. They do not have antigen presenting properties (but rather, requiring B cells or NK cells for its antigen-presenting property). They are called T cells because they mature in the thymus. T cells are capable of recognizing an antigen when displayed on the surface of antigen presenting cells or matrix together with one or more MHC molecules or one or more non-classical MHC molecules.

The terms "stimulating T cells" or "stimulation of T cells", as used herein, refer to the induction or activation of a T cell response by a primary signal, such as by the interaction with an antigen-MHC class II complex through the T cell antigen receptor. The term also includes the co-stimulation of T cells, such as through cytokines (e.g. CD80 or CD86 proteins). A T cell is activated if it has received a primary signaling event which initiates an immune response by the T cell.

The term "priming T cells", as used herein, refers to the induction of a first contact of the T cell with its specific antigen (e.g. by dendritic cells (DCs) presenting the antigen to T cells), which causes the differentiation of the T cell into an effector T cell (e.g. a cytotoxic T cell or a T helper cell).

The terms "expanding T cells" or "expansion of T cells", as used herein, refer to the increase of the number of T cells, preferably T cells specifically recognizing an antigen. It is preferred, that the number of T cells specifically recognizing the antigen comprised in the article of the present invention or the procession product of the antigen increases. The antigen or procession product of the antigen is preferably presented in the context of MHC molecules, such as on the surface of antigen presenting cells (APCs) like dendritic cells (DCs) or macrophages.

The term "immunotherapy", as used herein, relates to the treatment of a disease or condition by inducing, enhancing, or suppressing an immune response. Immunotherapies designed to elicit or amplify an immune response are classified as activation immunotherapies, while immunotherapies that reduce or suppress an immune response are classified as suppression immunotherapies. The term "immunotherapy" includes antigen immunization or antigen vaccination as well as tumor immunization or tumor vaccination. The term "immunotherapy" also relates to the manipulation of immune responses such that inappropriate immune responses are modulated into more appropriate ones in the context of autoimmune diseases such as rheumatic arthritis, allergies, diabetes, or multiple sclerosis.

The terms "immunization" or "vaccination", as used herein, describe the process of administering an antigen to an individual with the purpose of inducing an immune response, for example, for therapeutic or prophylactic reasons.

The term "therapeutic treatment", as used herein, relates to any treatment which improves the health status and/or prolongs (increases) the lifespan of an individual. Said treatment may eliminate the disease in an individual, arrest, inhibit, or slow the development of a disease in an individual, decrease the frequency or severity of symptoms in an individual, and/or decrease the recurrence in an individual who currently has or who previously has had a disease.

The terms "prophylactic treatment" or "preventive treatment", as used herein, relate to any treatment that is intended to prevent a disease from occurring in an individual. The terms "prophylactic treatment" or "preventive treatment" are used herein interchangeably.

The terms "protect", "prevent", "prophylactic", "preventive", or "protective", as used herein, relate to the prevention and/or treatment of the occurrence and/or the propagation of a disease, e.g. tumor, in an individual. For example, a prophylactic administration of an immunotherapy, e.g. by administering the article or the pharmaceutical composition of the present invention, can protect the receiving individual from the development of a tumor. For example, a therapeutic administration of an immunotherapy, e.g. by administering the article or the pharmaceutical composition of the present invention, can stop the development of a disease, e.g. lead to the inhibition of the progress/growth of a tumor. This comprises the deceleration of the progress/growth of the tumor, in particular a disruption of the progression of the tumor, which preferably leads to elimination of the tumor. A therapeutic administration of an immunotherapy may protect the individual from the dissemination or metastasis of existing tumors.

The terms "individual" and "subject" are used interchangeably in the context of the present invention. The individual or subject may be healthy, afflicted with a disease or disorder (e.g. cancer), or susceptible to a disease or disorder (e.g. cancer). The individual or subject may be an animal, e.g. a human. Preferably, the individual or subject is a human or another mammal (e.g. mouse, rat, rabbit, dog, cat, cattle, swine, sheep, horse or primate). Unless otherwise stated, the terms "individual" and "subject" do not denote a particular age and, thus, encompass adults, elderlies, children, and newborns. The "individual" or "subject" may be a "patient".

The term "patient", as used herein, means an individual or subject which is diseased, i.e. which suffers from a disease or disorder. The patient may be an animal, e.g. a human. Preferably, the animal is a human or another mammal (e.g. mouse, rat, rabbit, dog, cat, cattle, swine, sheep, horse or primate).

The article of the present invention may be administered in the form of any suitable pharmaceutical composition. Said pharmaceutical composition may further comprise adjuvants, pharmaceutical acceptable carriers, diluents, and/or excipients. Said pharmaceutical composition is useful for treating, preventing, or reducing the severity of a disease or disorder. It may be administered locally or systemically, preferably systemically.

The term "systemic administration", a used herein, refers to the administration of the article of the present invention such that the article becomes widely distributed in the body of an individual in significant amounts and develops a biological effect (or more specifically the antigen comprised therein). Typical systemic routes of administration include administration by introducing the article directly into the vascular system or oral, pulmonary, or intramuscular administration wherein the article is adsorbed, enters the vascular system, and is carried to one or more desired site(s) of action via the blood.

The systemic administration may be by parenteral administration. The term "parenteral administration", as used herein, refers to the administration of the article of the present invention such that the article does not pass the intestine. The term "parenteral administration" includes intravenous administration, subcutaneous administration, intradermal administration, or intraarterial administration, but is not limited thereto.

As mentioned above, the pharmaceutical compositions of the present invention may comprise adjuvants. The term "adjuvant", as used herein, relates to a compound, which, when administered in combination with an antigen or antigen peptide to an individual, prolongs, enhances, or accelerates an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells. Adjuvants comprise a heterogeneous group of compounds such as oil emulsions (e.g., Freund's adjuvants), mineral compounds (such as alum), bacterial products (such as Bordetella pertussis toxin), or immune-stimulating complexes. Examples for adjuvants include saponins, incomplete Freund's adjuvants, complete Freund's adjuvants, tocopherols, or aluminium, but are not limited thereto. However, adjuvants may also have negative side effects. Aluminium salt, for example, has the potential to cause severe local and systemic side-effects including sterile abscesses, eosinophilia and myofascitis, although fortunately most of the more serious side-effects are relatively rare. In addition, there is also community concern regarding the possible role of aluminium in neurodegenerative diseases such as Alzheimer's disease. Consequently, there is a major unmet need for safer and more effective adjuvants suitable for human use. The best would be, if the use of adjuvants would be superfluous.

The pharmaceutical composition according to the present invention is generally applied in a "pharmaceutically effective amount". The term "pharmaceutically effective amount", as used herein, refers to the amount which achieves a desired reaction or a desired effect alone or together with further doses. In case of the treatment of a particular disease, the desired reaction preferably relates to an inhibition of the course of the disease. This comprises slowing down the progress of the disease and, in particular, interrupting or reversing the progress of the disease. The desired reaction in a treatment of a disease may also be a delay of the onset or a prevention of the onset of the disease. An effective amount of the articles or compositions described herein will depend on the condition to be treated, the severeness of the disease, the individual parameters of the patient/subject, including age, physiological condition, size, and weight, the duration of treatment, the type of an accompanying therapy (if present), the specific route of administration, and similar factors. Accordingly, the doses of the articles or compositions described herein may depend on various of such parameters. In case that a reaction in the patient/subject is insufficient with an initial dose, higher doses (or effectively higher doses achieved by a different, more localized route of administration) may be used.

As mentioned above, the pharmaceutical composition of the present invention may further comprise pharmaceutical acceptable carriers, diluents, and/or excipients.

The term "excipient", as used herein, is intended to indicate all substances in a pharmaceutical composition which are not active ingredients such as binders, lubricants, thickeners, surface active agents, preservatives, emulsifiers, buffers, flavoring agents, or colorants.

The term "diluent", as used herein, relates to a diluting and/or thinning agent. Moreover, the term "diluent" includes a solution, suspension (e.g. liquid or solid suspension) and/or media.

The term "carrier", as used herein, relates to one or more compatible solid or liquid fillers, which are suitable for an administration, e.g. to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol, and water.

Pharmaceutical carriers, diluents, and/or excipients can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose, and polyethylene glycol. Examples of suitable lubricants include sodium oleate, sodium stearate, magnesium stearate, sodium benzoate, sodium acetate, sodium chloride, and the like. Preservatives, stabilizers, dyes, and even flavoring agents may be provided in the pharmaceutical composition. Examples of preservatives include sodium benzoate, sorbic acid, and esters of p-hydroxybenzoic acid. Antioxidants and suspending agents may be also used.

In the context of the present invention, the term "particle" refers to a structured entity formed by polypeptides. According to the present invention, the structured entity formed by polypeptides comprises silk polypeptides and antigens. In one embodiment, the particle comprises a fusion or hybrid polypeptide comprising a silk polypeptide and an antigen. In one preferred embodiment, the particle comprises a fusion or hybrid polypeptide comprising a silk polypeptide, an antigen, and an enzymatically cleavable linker, wherein the antigen is connected to the silk polypeptide via the enzymatically cleavable linker or wherein the enzymatically cleavable linker is located between the silk polypeptide and the antigen.

The term "particle", as used herein, further refers to a micro- or nano-sized spherical structure which may be formed by protein aggregation under certain conditions. It is preferred that the particle comprises or consists of a matrix and a surface. Preferably, the matrix is homogenous, more preferably without any clear visible inclusions (e.g. determined via electron microscopy). In this respect, it should be noted that said inclusions may be air and polypeptides which are not related to the polypeptides of the present invention.

The term "surface", as used herein, defines the outer sphere of the particle, which includes those sphere sections that are directly exposed to the surrounding space, e.g. surrounding medium or body liquid. Although the particle appears rather smooth and uniform, its surface on the sub-microscopic level reveal a thin mantle with irregular and diffuse structures. A surface, thus, delineates the outermost layer of the particle which shares an interface with the surrounding space, e.g. surrounding medium or body liquid.

The term "matrix", as used herein, defines the inner sphere of the particle, which is not the surface, i.e. which, according to the above definition, does not include any interface to the surrounding space, e.g. surrounding medium or body liquid. The matrix is to be understood as a solid sphere having a radius and accordingly a volume usually smaller than that of the particle. The volume of the matrix is usually more than 50% of the total volume, preferably more than 60%, 70%, 80%, 90%, most preferably more than 95%, e.g. more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%.

The terms "aggregation" or "phase separation", as used herein, refer to particle formation due to a salting-out mechanism which in particular can be considered as a liquid-liquid phase separation. The "one-phase state" is the initial state displayed by a solution of monomeric and intrinsically unfolded protein molecules. For example, changing constraints such as the ionic strength by addition of kosmotropic ions alters the free energy of the system and leads to phase separation into protein-rich and solvent-rich phases. This phase-separated state is energetically favoured and the protein concentration in the "protein phase" increases to a critical level. Upon reaching the critical concentration for nucleation, several structured nuclei are formed simultaneously in the protein-rich phase. The nuclei start to grow in a spherical manner, interacting with additional monomers and thereby converting their structure. Spherical growth stops when the protein concentration in the protein-rich phase is below the equilibrium of solubility. Hence the sphere size does not increase further. Phase separation, thus, means that protein-rich and solvent-rich phases are separated. Without being bound to a theory, the sphere size is generally dependent on protein concentration and mixing conditions. There exist however various other methods in the art for triggering aggregation of proteins.

The process of microsphere assembly is typically monitored by light-scattering after initiation of aggregation. In particular, the colloidal stability of the resulting particles can be analysed by measuring the intensity of scattered light at a certain wavelength. Also the mean particle size and particle size distribution can be determined by laser diffraction, also called static light scattering (SLS).

The obtained particles may also be analysed using methods such as scanning electron microscopy (SEM) and Fourier transform infrared spectroscopy (FTIR). A further description of these methods can be found in the description and in the examples below.

After phase separation, the produced particles can be separated by routine methods such as centrifugation, filtration, or sedimentation. The prepared particles may subsequently be washed and/or stored, for example, in a dried or lyophilized form.

The term "net charge of the surface of the particle" relates to the total sum of charges, such as positive and negative charges, at the surface of the particle. For example, if the particle comprises on its surface a higher number of negative charges than positive charges, the net charge of the surface of the particle is negative. If the particle comprises on its surface a higher number of positive charges than negative charges, the net charge of the surface of the particle is positive. If the particle comprises on its surface an equal number of positive charges and negative charges, the net charge of the surface of the particle is neutral, particularly electroneutral. Thus, the net charge of the surface of the particle according to the present invention can be negative, positive, or neutral. Preferably, the particle of the present invention has a net negative surface charge.

The term "average diameter" refers to the mean diameter of the particles and may be calculated by dividing the sum of the diameter of each particle by the total number of particles. Although the term "diameter" is used normally to refer to the maximal length of a line segment passing through the center and connecting two points on the periphery of a spherical object, it is also used herein to refer to the maximal length of a line segment passing through the center and connecting two points on the periphery of particles having a substantial spherical shape or other shapes.

The term "protease (also designated as peptidase or proteinase)", as used herein, refers to any enzyme that performs proteolysis, that is, begins protein catabolism by hydrolysis of the peptide bonds that link amino acids together in a polypeptide chain. Proteases have evolved multiple times, and different classes of protease can perform the same reaction by completely different catalytic mechanisms. Proteases can be found in animals, plants, bacteria, archaea and viruses.

The term "cathepsin (CTS)", as used herein, refers to a protease (enzymes that degrade proteins) which is found in all animals as well as other organisms. Different family members exists, which are distinguished by their structure, catalytic mechanism, and which proteins they cleave. Most of the members become activated at the low pH found in lysosomes. Thus, the activity of this family lies almost entirely within those organelles. Cathepsin may be cathepsin A, cathepsin B, cathepsin C, cathepsin D, cathepsin E, cathepsin F, cathepsin G, cathepsin H, cathepsin K, cathepsin L1, cathepsin L2, cathepsin O, cathepsin S, cathepsin W, or cathepsin Z. Preferably, the cathepsin is cathepsin S or B. More preferably, cathepsin is cathepsin S.

In one embodiment, the polypeptide of the present invention or the polypeptide used in the present invention comprises a protease cleavable linker, e.g. a cathepsin S cleavable linker or cathepsin B cleavable linker. Preferably, the cathepsin S cleavable linker has the sequence according to SEQ ID NO: 1 or is a variant thereof or has the sequence according to SEQ ID NO: 2 or is a variant thereof, or the cathepsin B cleavable linker has the sequence according to SEQ ID NO: 2 or is a variant thereof. In this respect, it should be noted that cathepsin S is able to cleave its own cleavage sites (comprised in SEQ ID NO: 1) and also the cleavage sites which are usually cleaved by cathepsin B (comprised in SEQ ID NO: 2). The sequence according to SEQ ID NO: 1 (GPMGLPG) comprises the cleavage site PMGLP (SEQ ID NO: 20) and the sequence according to SEQ ID NO: 2 (GAVGFLGIG) comprises the cleavage site GFLG (SEQ ID NO: 21). Instead of the cleavage site GFLG (SEQ ID NO: 21), the dipeptide sequence Val-Cit, or the tetra peptides ALAL (SEQ ID NO: 22) or GGGF (SEQ ID NO: 23) can be used as cathepsin B cleavage sites. The cleavage sites Val-Cit, ALAL (SEQ ID NO: 22), or GGGF (SEQ ID NO: 23) may be effective in combination with the C16 CathBseq-SIINFEKL (SEQ ID NO: 15) particles. In this case, the cleavage site GFLG (SEQ ID NO: 21) within the sequence according to SEQ ID NO: 15 is replaced by Val-Cit, ALAL (SEQ ID NO: 22), or GGGF (SEQ ID NO: 23). It is also possible that the cathepsin cleavable linker comprised in the polypeptide of the present invention consists of the cleavage site Val-Cit or the cleavages sites according to SEQ ID NO: 20 to 23.

Embodiments of the Invention

The inventors of the present patent application surprisingly found that antigens which are part of articles, e.g. particles, comprising silk polypeptides are preferentially taken up by animal cells, e.g. human cells. In this context, the inventors of the present patent application were surprised that the articles, e.g. particles, which are mainly composed of silk, function as an auxiliary material which stabilizes the antigen and makes it transportable. The articles, e.g. particles, can be degraded within the organism (e.g. human body) without traces. The articles, e.g. particles, are non-toxic, in particular non-cytotoxic, and non-immunogenic.

Thus, in a first aspect, the present invention relates to a polypeptide comprising
(i) a silk polypeptide and
(ii) an (polypeptide) antigen.

The polypeptide may be a molecule which is composed of at least two components which can either be translated as a single chain polypeptide from the same mRNA molecule or can be produced by separate translation of the at least two components and subsequent coupling, e.g. by chemical reactions. In the first case, the silk polypeptide is fused/attached to the antigen. In the second case, the silk polypeptide is linked/coupled to the antigen. Preferably, the polypeptide is a single chain polypeptide which may also be designated as a hybrid polypeptide or fusion polypeptide.

In one preferred embodiment, the polypeptide further comprises an enzymatically cleavable linker. Said linker may be any linker which is cleavable by an enzyme. When the enzymatically cleavable linker is present, the antigen is connected to the silk polypeptide via said linker or said linker is located between the silk polypeptide and the antigen. If the polypeptide is produced as a single chain polypeptide (which may also be designated as a hybrid polypeptide or fusion polypeptide), the antigen is attached/fused to the silk polypeptide via the enzymatically cleavable linker. If the polypeptide is produced by separate translation of at least two components and subsequent coupling, e.g. by chemical reactions, the antigen is linked/coupled to the silk polypeptide via the enzymatically cleavable linker. It is particularly preferred that the enzymatically cleavable linker is intracellularly cleavable by an enzyme, e.g. within the host cell.

Preferably, the enzymatically cleavable linker is a protease cleavable linker. Said linker may be any linker which is cleavable by a protease.

More preferably, the protease cleavable linker is a cathepsin cleavable linker. The cathepsin may be cathepsin A, cathepsin B, cathepsin C, cathepsin D, cathepsin E, cathepsin F, cathepsin G, cathepsin H, cathepsin K, cathepsin L1, cathepsin L2, cathepsin O, cathepsin S, cathepsin W, or cathepsin Z. The cathepsin cleavable linker may be a cathepsin A, cathepsin B, cathepsin C, cathepsin D, cathepsin E, cathepsin F, cathepsin G, cathepsin H, cathepsin K, cathepsin L1, cathepsin L2, cathepsin O, cathepsin S, cathepsin W, or cathepsin Z cleavable linker.

Even more preferably, the cathepsin cleavable linker is a cathepsin B cleavable linker or a cathepsin S cleavable linker. The cathepsin S cleavable linker is particularly preferred.

Cathepsin B is a member of the peptidase C1 family. It is a lysosomal cysteine protease with both endopeptidase and exopeptidase activity. It plays a role in protein turnover. It is also known as amyloid precursor protein secretase and is involved in the proteolytic processing of amyloid precursor protein (APP). Cathepsin B is ubiquitously expressed in almost every tissue. In contrast thereto, cathepsin S is only expressed in certain tissues. In particular, cathepsin S is expressed by antigen presenting cells including macrophages, B-lymphocytes, dendritic cells, and microglia. In addition, cathepsin S is expressed by some epithelial cells. Cathepsin S is also a member of the peptidase C1 family. It is a lysosomal cysteine protease. It plays a key role in the degradation of antigenic proteins and their further processing via the MHC class II pathway. Cathepsin S is able to cleave its own cleavage sites (see, for example, SEQ ID NO: 1) and also the cleavage sites which are usually cleaved by cathepsin B (see, for example, SEQ ID NO: 2). In this respect, it should be noted that cathepsin S cleaves the cleavage sites which are usually cleaved by cathepsin B slower and in a less extent.

Most preferably,
(i) the cathepsin S cleavable linker has the sequence according to SEQ ID NO: 1 or is a variant thereof or has the sequence according to SEQ ID NO: 2 or is a variant thereof, or
(ii) the cathepsin B cleavable linker has the sequence according to SEQ ID NO: 2 or is a variant thereof.

The inventors of the present patent application found that cathepsin S is able to cleave a cathepsin S cleavable linker, e.g. a cathepsin S cleavable linker having the sequence according to SEQ ID NO: 1, as well as a cathepsin B cleavable linker, e.g. a cathepsin B cleavable linker having the sequence according to SEQ ID NO: 2.

A SEQ ID NO: 1 or SEQ ID NO: 2 variant differs from the reference sequence from which it is derived by up to 1, 2, 3, or 4 amino acid changes in the amino acid sequence (i.e. substitutions, additions, insertions, deletions, N-terminal truncations and/or C-terminal truncations). Such a variant can alternatively or additionally be characterised by a certain degree of sequence identity to the reference module from which it is derived. Thus, a SEQ ID NO: 1 or SEQ ID NO: 2 variant has a sequence identity of at least 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference sequence. Preferably, the sequence identity is over the whole length of the respective sequence.

A fragment (or deletion variant) of SEQ ID NO: 1 or SEQ ID NO: 2 has preferably a deletion of up to 1, 2, 3, or 4 amino acids at its N-terminus and/or at its C-terminus. The deletion can also be internally.

Additionally, the SEQ ID NO: 1 or SEQ ID NO: 2 variant or fragment is only regarded as a SEQ ID NO: 1 or SEQ ID NO: 2 variant or fragment within the context of the present invention, if the modifications with respect to the amino acid sequence on which the variant or fragment is based do not negatively affect the ability of cathepsin, e.g. cathepsin S or B, to cleave this sequence. The skilled person can readily assess whether cathepsin S or B is still capable of cleaving the SEQ ID NO: 1 or SEQ ID NO: 2 variant, e.g. by performing an enzyme assay on a test substrate comprising the modified sequence.

The silk polypeptide may be a spider silk polypeptide, e.g. a major ampullate silk polypeptide such as a dragline silk polypeptide, a minor ampullate silk polypeptide, or a flagelliform silk polypeptide of an orb-web spider (e.g. Araneidae or Araneoids), an insect silk polypeptide, a mussel byssus silk polypeptide, or a mixture thereof. The orb-web spider may be selected from the group consisting of *Araneus diadematus*, *Nephila clavipes*, and *Latrodectus hesperus*. The insect silk polypeptide may be of *Lepidoptera*, particularly Bombycidae such as *Bombyx mori*. The insect silk polypeptide may also be of Hymenoptera, particularly Apoidea such as Anthophila. Preferably, the silk polypeptide is a spider silk polypeptide.

It is preferred that the silk polypeptide is a polypeptide with an amino acid sequence which comprises or consists of at least 50%, 60%, 65%, 70%, 75%, 80%, 85%, or 90% multiple copies of repetitive units. It is more preferred that the silk polypeptide is a polypeptide with an amino acid sequence which comprises or consists of at least 95% multiple copies of repetitive units. Said repetitive units may be identical or different. It is particularly preferred that the silk polypeptide comprises at least two identical repetitive units. For example, the silk polypeptide may comprise between 2 to 100 repetitive units, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 repetitive units.

It is further (alternatively or additionally) preferred that the silk polypeptide consists of between 40 to 3000 amino acids. It is more preferred that the silk polypeptide consists of between 40 to 1500 amino acids. It is even more preferred that the silk polypeptide consists of between 200 to 1200 amino acids. It is most preferred that the silk polypeptide consists of between 250 to 600 amino acids.

It is also (alternatively or additionally) preferred that the silk polypeptide is a recombinant silk polypeptide.

As mentioned above, it is particularly preferred that the silk polypeptide comprises at least two identical repetitive units. In one embodiment, the repetitive units are independently selected from the group consisting of module C (SEQ ID NO: 3) or a variant thereof, module $C^{Cys}$ (SEQ ID NO: 4), and module $C^{kappa}$ (SEQ ID NO: 18). Module $C^{Cys}$ (SEQ ID NO: 4) is a variant of module C (SEQ ID NO: 3). In this module, the amino acid S (Ser) at position 25 has been replaced by the amino acid C (Cys). Module $C^{kappa}$ (SEQ ID NO: 18) is also a variant of module C (SEQ ID NO: 3). In this module, the amino acid E (Glu) at position 20 has been replaced by the amino acid K (Lys).

The module C variant differs from the reference module C from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference module from which it is derived. Thus, the module C variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference module C. Preferably, the sequence identity is over a continuous stretch of at least 5, 10, 15, 18, 20, 24, 27, 28, 30, 34, 35, or more amino acids, preferably over the whole length of the respective reference module C.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference module C. It is further particularly preferred that the sequence identity is at least 80% over a continuous stretch of at least 5, 10, 15, 18, 20, 24, 28, or 30 amino acids, is at least 85% over a continuous stretch of at least 5, 10, 15, 18, 20, 24, 28, or 30 amino acids, is at least 90% over a continuous stretch of at least 5, 10, 15, 18, 20, 24, 28, or 30 amino acids, is at least 95% over a continuous stretch of at least 5, 10, 15, 18, 20, 24, 28, or 30 amino acids, is at least 98% over a continuous stretch of at least 5, 10, 15, 18, 20, 24, 28, or 30 amino acids, or is at least 99% over a continuous stretch of at least 5, 10, 15, 18, 20, 24, 28, or 30 amino acids of the respective reference module C.

A fragment (or deletion) variant of module C has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module C variant or fragment is only regarded as a module C variant or fragment within the context of the present invention, if the modifications with respect to the amino acid sequence on which the variant or fragment is based do not negatively affect the ability of the silk polypeptide to internalize the antigen into the target cell. The skilled person can readily assess whether the silk polypeptide comprising a module C variant or fragment is still capable of internalizing the antigen into the target cell, e.g. by culturing target cells, e.g. BMDCs, with fluorescently-labelled, e.g. FITC-labelled, spider silk particles comprising the antigen and conducting flow cytometry analysis (see example 11 of the experimental section).

$C^{Cys}$ or $C^{kappa}$ variants may also be encompassed by the present invention. Regarding the $C^{Cys}$ or $C^{kappa}$ variants, the same explanations/definitions apply which have been made with respect to the module C variant (see above).

The use of a positively charged protein such as $C^{kappa}$ (SEQ ID NO: 18) in contrast to the use of module C (SEQ ID NO: 3) or a variant thereof results in a positive surface charge of the articles at neutral pH. The positive surface charge can improve the uptake into cells.

It is also particularly preferred that the silk polypeptide comprises at least one non-repetitive (NR) unit. Said non-repetitive (NR) unit may be comprised at the N- and/or C-terminus. In one embodiment, the NR unit is selected from the group consisting of NR3 (SEQ ID NO: 7) or a variant thereof, NR4 (SEQ ID NO: 8) or a variant thereof, NR5 (SEQ ID NO: 9) or a variant thereof, and NR6 (SEQ ID NO: 10) or a variant thereof. The NR3 (SEQ ID NO: 7) unit is based on the amino acid sequence of ADF-3 of the spider *Araneus diadematus* and the NR4 (SEQ ID NO: 8) unit is based on the amino acid sequence of ADF-4 of the spider *Araneus diadematus* (WO 2006/008163). In addition, the NR5 (SEQ ID NO: 9) unit and the NR6 (SEQ ID NO: 10) unit are derived from *Latrodectus hesperus*.

Regarding the NR3, NR4, NR5, or NR6 unit variant, the same explanations/definitions apply which have been made with respect to the module C variant (see above).

In addition, a NR3, NR4, NR5, or NR6 unit variant or fragment is only regarded as a NR3, NR4, NR5, or NR6 unit variant or fragment within the context of the present invention, if the modifications with respect to the amino acid sequence on which the variant or fragment is based do not negatively affect the ability of the silk polypeptide to internalize the antigen into the target cell. The skilled person can readily assess whether the silk polypeptide comprising a NR3, NR4, NR5, or NR6 unit variant or fragment is still capable of internalizing the antigen into the target cell, e.g. by culturing target cells, e.g. BMDCs, with fluorescently-labelled, e.g. FITC-labelled, spider silk particles comprising the antigen and conducting flow cytometry analysis (see example 11 of the experimental section).

It is further particularly preferred that the silk polypeptide comprises at least one Tag (sequence). The Tag may be comprised at the N- and/or C-terminus. The Tag is preferably non-repetitive. It is suitable for the purification and/or detection of the silk polypeptide. The Tag may be a His-Tag or a T7-Tag. Preferably, the T7-Tag has a sequence according to SEQ ID NO: 5 or a sequence according to SEQ ID NO: 6.

In one preferred embodiment, the silk polypeptide is selected from the group consisting of $(C)_m$, $(C^{Cys})_m$, ($C^{kappa}$)$_m$, (C)$_m$C$^{Cys}$, C$^{Cys}$(C)$_m$, (C)$_m$C$^{Cys}$(C)$_m$, (C)$_m$NR$_z$, NR$_z$(C)$_m$ and NR$_z$(C)$_m$NR$_z$, wherein m is an integer of 8 to 96, i.e. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or 96, z is an integer of 1 to 3, i.e. 1, 2, or 3, and NR stands for a non-repetitive unit.

In one more preferred embodiment, the silk polypeptide is selected from the group consisting of $C_8$, $C_{16}$, $C_{32}$, $C_{48}$, $C^{kappa}_8$, $C^{kappa}_{16}$, $C^{kappa}_{32}$, $C^{kappa}_{48}$, $C_8 C^{Cys}$, $C_{16} C^{Cys}$, $C_{32} C^{Cys}$, and $C48 C^{Cys}$.

Preferably, the antigen is a disease-associated antigen. More preferably, the antigen, in particular the disease-associated antigen, is selected from the group consisting of a viral antigen, a microbial antigen, such as a bacterial or fungal antigen, a zooparasitic antigen, and a tumor antigen.

As an exemplarily antigen, the inventors of the present patent application used an epitope of chicken-Ovalbumin (OVA$_{257-264}$) with the amino acid sequence SIINFEKL (SEQ ID NO: 11). The chicken-Ovalbumin epitope with the amino acid sequence SIINFEKL (SEQ ID NO: 11) was selected, because it is the best characterized and generally applied system to demonstrate/monitor the effect of peptide-epitopes to an immune reaction. This chicken-Ovalbumin epitope system with the amino acid sequence SIINFEKL (SEQ ID NO: 11) is a state of the art-tool and resembles a universally valid example for the presentation of a plethora of antigens to the immune system. For the experiments shown herein, the inventors of the present patent application used a recombinant spider silk polypeptide comprising $C_{16}$ having the sequence according to SEQ ID NO: 12. The inventors of the present patent application recombinantly produced different polypeptides comprising a silk polypeptide and an antigen or a silk polypeptide, an enzymatically cleavable linker, and an antigen. The polypeptide comprising the spider silk polypeptide $C_{16}$ and an epitope of chicken-Ovalbumin (OVA$_{257-264}$) has the sequence according to SEQ ID NO: 13. The polypeptide comprising the spider silk polypeptide $C_{16}$, a cathepsin S cleavable linker, and an epitope of chicken-Ovalbumin (OVA$_{257-264}$) has the sequence according to SEQ ID NO: 14. The polypeptide comprising the spider silk polypeptide $C_{16}$, a cathepsin B cleavable linker, and an epitope of chicken-Ovalbumin (OVA$_{257-264}$) has the sequence according to SEQ ID NO: 15.

In a second aspect, the present invention relates to a nucleic acid molecule encoding the polypeptide of the first aspect.

It is preferred that the nucleic acid molecule is comprised in a vector. The vector may be any vector known to the skilled person. For example, the vector may be a plasmid vector, a viral vector such as an adenoviral or a baculoviral vector, a cosmid vector, or a phage vector such as a lambda phage vector. Said vectors include expression as well as cloning vectors. Expression vectors generally contain a desired coding sequence and appropriate DNA sequences to control the expression of the operably linked coding sequence in a particular host organism (e.g., bacteria, yeast, plant, insect, or mammal) or in in vitro expression systems. Expression control sequences may be sequences which control (i) the expression, e.g. promoters, TATA-box, enhancers, (ii) post-transcriptional events, e.g. polyadenylation, and (iii) the translation of nucleic acid sequences. Cloning vectors are generally used to engineer and amplify a certain desired DNA fragment and may lack functional sequences needed for expression of the desired DNA fragments. The above-mentioned vectors are preferably recombinant vectors.

The cell may be transformed, transfected, or infected with the nucleic acid molecule or the vector comprising the nucleic acid molecule. The cell can be used for expressing the nucleic acid molecule or amplifying the nucleic acid molecule or the vector comprising the nucleic acid molecule. The cell may be a prokaryotic or eukaryotic cell. The prokaryotic cell may be a *E. coli* cell or a *Bacillus subtilis* cell. The eukaryotic cell may be a mammalian cell, a plant cell, a yeast cell, or an insect cell. The mammalian cell may be a CHO, COS, HeLa, 293T, HEH, or BHK cell. The yeast cell may be a *Saccharomyces cerevisiae* cell, a *Schizosaccharomyces pombe* cell, a *Pichia pastoris* cell, a *Candida albicans* cell, or a *Hansenula polymorpha* cell. The insect cell may be a *Lepidoptera* insect cell. The plant cell may be a tobacco cell, a potato cell, a corn cell, a pea cell, or a tomato cell. The above-mentioned cells may also be named host cells. They are preferably recombinant cells.

In a third aspect, the present invention relates to a method for producing a polypeptide comprising the step of:
(a) expressing the nucleic acid molecule of the second aspect in a cell, thereby producing the polypeptide in the cell.

The cell may also be named host cell. The cell may be a prokaryotic or eukaryotic cell. The prokaryotic cell may be a *E. coli* cell or a *Bacillus subtilis* cell. The eukaryotic cell may be a mammalian cell, a plant cell, a yeast cell, or an insect cell. The mammalian cell may be a CHO, COS, HeLa, 293T, HEH, or BHK cell. The yeast cell may be a *Saccharomyces cerevisiae* cell, a *Schizosaccharomyces pombe* cell, a *Pichia pastoris* cell, a *Candida albicans* cell, or a *Hansenula polymorpha* cell. The insect cell may be a *Lepidoptera* insect cell. The plant cell may be a tobacco cell, a potato cell, a corn cell, a pea cell, or a tomato cell. The above-mentioned cells are preferably recombinant cells.

The nucleic acid molecule may be found inside the cell (i) freely dispersed as such, (ii) incorporated in a vector, or (iii) integrated into the cell genome or mitochondrial DNA. Preferably, the vector, e.g. plasmid or viral vector, is an expression vector.

The cell may be transformed, transfected, or infected with the nucleic acid molecule or the vector comprising the nucleic acid molecule.

Preferably, the method further comprises the step of:
(b) isolating the polypeptide from the cell.

The isolation of the polypeptide from the cell may be achieved by separating said polypeptide from said cell via centrifugation, sedimentation, and/or filtration, e.g. via centrifugation and filtration, via sedimentation and filtration, via sedimentation and centrifugation, or via centrifugation, sedimentation, and filtration. Depending on the polypeptide to be harvested, the parameters for centrifugation, sedimentation, or filtration may vary. The person skilled in the art is able to easily adapt the appropriate separation parameters, e.g. the acceleration-force/G-force and/or time using centrifugation for separation, filter size using filtration for separation, and/or sedimentation time using sedimentation for separation, in order to harvest said polypeptide produced by said cells.

After step (b), further purification of the isolated polypeptide may be required. Said purification may be achieved via chromatography, preferably column chromatography, more preferably size exclusion chromatography, hydrophobic interaction chromatography, ion exchange chromatography, affinity chromatography, or high pressure liquid chromatography, electrophoresis, preferably gel electrophoresis, or ultracentrifugation. A preferred isolation method for the production of polypeptides is described in WO 2011/120690 A2.

In one preferred embodiment, the purified polypeptide is endotoxin free. Endotoxin depletion is achieved by filtration, steam sterilisation (e.g. in an autoclave), or a combination of both, i.e. filtration and steam sterilisation (e.g. in an autoclave).

In a fourth aspect, the present invention relates to an article comprising the polypeptide of the first aspect. The article may also be named antigen carrier or antigen carrier vehicle.

The article may be selected from the group consisting of a particle, capsule, fiber, film, granule, gel, fabric made of fibers, rod or bundles thereof. Preferably, the rod comprises or consists of fibers. Preferably, the fabric is a woven or non-woven fabric. It is preferred that said article is not cytotoxic and not immunogenic. It is further (alternatively or additionally) preferred that said article is sterilizable.

Preferably, said article is a particle. It is preferred that the particle is not cytotoxic and not immunogenic. It is further (alternatively or additionally) preferred that the particle is sterilizable. The particle is preferably a nanoparticle, because cellular uptake is a major aspect of its action path and, therefore, desirable.

In one embodiment, the particle has an average diameter in the range of from 50 nm to 1000 nm, e.g. from 100 nm to 900 nm, from 200 nm to 800 nm, from 200 to 700 nm, from 300 to 600 nm, from 300 nm to 500 nm, or from 300 nm to 400 nm. The range of from 250 to 520 nm is particularly preferred.

In one further embodiment, the particle has an average diameter of at least 50 nm, at least 60 nm, at least 70 nm, at least 80 nm, at least 90 nm, at least 100 nm, at least 150 nm, at least 200 nm, at least 250 nm, at least 300 nm, at least 400 nm, at least 500 nm, at least 600 nm, at least 700 nm, at least 800 nm, at least 900 nm, and/or the particle has an average diameter of no more than 1000 nm, no more than 900 nm, no more than 800 nm, no more than 700 nm, no more than 600 nm, no more than 520 nm, no more than 500 nm, no more than 400 nm, no more than 300 nm, no more than 250 nm, no more than 200 nm, no more than 150 nm, no more than 100 nm, no more than 90 nm, no more than 80 nm, no more than 70 nm, no more than 60 nm.

In one preferred embodiment, the particle has an average diameter (i) in the range of from 50 nm to 400 nm, preferably from 50 nm to 200 nm, or (ii) in the range of from 200 nm to 1000 nm, preferably from 200 nm to 800 nm, more preferably from 250 nm to 520 nm or from 300 nm to 600 nm.

In a fifth aspect, the present invention relates to a method for producing an article comprising the steps of:
(a) providing an aqueous solution comprising the polypeptide of the first aspect, and
(b) forming an article out of/from the solution provided in (a).

Said article may also be named antigen carrier or antigen carrier vehicle.

As the silk polypeptide and the antigen are part of the same polypeptide, no additional loading step is necessary after article formation.

The articles, which are mainly composed of silk, function as an auxiliary material which stabilizes the antigen and makes it transportable. The articles can be degraded within the organism (e.g. human body) without traces.

The above-described article formation process does not require organic solvents. The avoidance of organic solvents has the advantage that organic solvent sensitive antigens retain their characteristic properties.

Preferably, the concentration of the polypeptide in the aqueous solution is between 0.1 wt %/vol and 30 wt %/vol, more preferably between 1 wt %/vol and 20 wt %/vol, even more preferably between 1 wt %/vol and 20 wt %/vol, and most preferably between 2 to 8 wt %/vol or 4 to 6 wt %/vol. Thus, for example, the concentration of the polypeptide in the aqueous solution is 0.1, 0.4, 0.6, 0.8, 1.0, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 9.0, 10.0, 12.0, 15.0, 18.0, 20.0, 25.0, or 30.0 wt %/vol.

The aqueous solution may be a buffered aqueous solution or water ($H_2O$) such as technical $H_2O$ or deionized $H_2O$. The buffered aqueous solution may be, for example, Tris/HCl. Preferably, the pH of the buffered aqueous solution is between pH 5.0 and pH 9.0, more preferably between pH 6.0 and pH 8.0, and even more preferably between pH 6.7 and pH 7.2, e.g. Tris/HCl, pH 7.0, pH 7.5, or pH 8.0. Preferably, the buffered aqueous solution is a solution between 10 and 100 mM Tris/HCl, more preferably between 10 and 50 mM Tris/HCl, and most preferably between 10 and 20 mM Tris/HCl, e.g. 10, 15, 20, 25, 30, 35, 40, 45, 50, 55, 60, 65, 70, 75, 80, 85, 90, 95, or 100 mM Tris/HCl.

Said article may be selected from the group consisting of a particle, capsule, fiber, film, granule, gel, fabric made of fibers, rod or bundles thereof. Preferably, the rod comprises or consists of fibers. Preferably, the fabric is a woven or non-woven fabric. It is preferred that said article is not cytotoxic and not immunogenic. It is further (alternatively or additionally) preferred that said article is sterilizable.

In one embodiment, the article is a particle. It is preferred that the particle is not cytotoxic and not immunogenic. It is further (alternatively or additionally) preferred that the particle is sterilizable. Generally, starting from an aqueous solution, aggregation of the polypeptide can be triggered under certain conditions to form particles. When the article is a particle, step (b) comprises triggering aggregation of the polypeptide. Thus, in one preferred embodiment, the method is for producing a particle and comprises the steps of:
(a) providing an aqueous solution comprising the polypeptide of the first aspect, and
(b) forming a particle out of/from the solution provided in (a), wherein said formation comprises triggering aggregation of the polypeptide.

The aggregation may be triggered by pH shift, ion exchange, shear forces, the addition of alcohol, the addition of a salt, the removal of water, temperature change, and by combinations thereof.

The alcohol may be ethanol or methanol. The salt is preferably a lyotropic salt. The lyotropic salt may be selected from the group consisting of ammonium sulphate, sodium phosphate, and potassium phosphate.

In one further (alternatively or additionally) preferred embodiment, the method further comprises the step of:
(c) separating the particle by phase separation.

After phase separation, the produced particles can be further separated by routine methods such as centrifugation, sedimentation, and/or filtration.

The particle size may be optimized by adjusting one or more of the following parameters: silk polypeptide and/or salt concentration, temperature during preparation, mixing intensity, and/or organic or aqueous solvents used for protein precipitation. Alternatively or additionally, the particle size may be optimized by adjusting the geometry of the mixing device like stirrer, static mixer or the like.

The prepared particles may subsequently be washed. The particles may also be stored, for example, in a dried or lyophilized form. The processes may be carried out under aseptic conditions.

The particle is preferably a nanoparticle, because cellular uptake is a major aspect of its action path and, therefore, desirable.

In one alternative embodiment, the article is a fiber. In this case, the aqueous solution may also be named spinning solution. It is preferred that the fiber is not cytotoxic and not immunogenic. It is further (alternatively or additionally) preferred that the fiber is sterilizable. When the article is a fiber, step (b) comprises drawing a fiber from the aqueous solution/spinning solution, or extruding and drawing a fiber from the aqueous solution/spinning solution. Thus, in one preferred embodiment, the method is for producing a fiber and comprises the steps of:

(a) providing an aqueous solution comprising the polypeptide of the first aspect, and
(b) forming a fibre out of/from the solution provided in (a), wherein said formation comprises drawing a fiber from the aqueous solution/spinning solution, or extruding and drawing a fiber from the aqueous solution/spinning solution.

Spinning methods such as wet spinning or electrospinning methods are known to the skilled person. For example, the aqueous solution/spinning solution is extruded through a spinneret to form a fiber. The resulting fiber can further be drawn or stretched. Whenever both crystalline and amorphous arrangements of the molecules exist in fibers, drawing or stretching will apply shear stress sufficient to orient the molecules to make them more parallel to the walls of the fiber and increase the tensile strength and toughness of the fiber.

The fiber may be used to make a fabric, e.g. a woven or non-woven fabric. The skilled person is aware of techniques allowing to generate a fabric, e.g. weaving processes. Thus, in an alternative embodiment, the article may be a fabric made of fibers. The fibers may also be part of a rod. Preferably, the rod comprises or consists of fibers. Bundles of rods may also be encompassed by the present invention.

In one alternative embodiment, the article is a film. In this case, the aqueous solution may also be named casting solution. It is preferred that the film is not cytotoxic and not immunogenic. It is further (alternatively or additionally) preferred that the film is sterilizable. When the article is a film, step (b) comprises casting an aqueous solution/a casting solution comprising the polypeptide onto a substrate. Thus, in one preferred embodiment, the method is for producing a film and comprises the steps of:

(a) providing an aqueous solution comprising the polypeptide of the first aspect, and
(b) forming a film out of/from the solution provided in (a), wherein said formation comprises casting an aqueous solution/a casting solution comprising the polypeptide onto a substrate.

In one further (alternatively or additionally) preferred embodiment, the method further comprises the step of:
(c) separating/removing the film from the substrate.

In one alternative embodiment, the article is a capsule. It is preferred that the capsule is not cytotoxic and not immunogenic. It is further (alternatively or additionally) preferred that the capsule is sterilizable.

When the article is a capsule, step (b) comprises generating an emulsion of at least two phases, said emulsion containing the solution provided in (a) as a first phase and at least one further phase, which is substantially immiscible with said first phase, and forming a polymer network of the polypeptide at the interface of the at least two phases. Thus, in one preferred embodiment, the method is for producing a capsule and comprises the steps of:

(a) providing an aqueous solution comprising the polypeptide of the first aspect, and
(b) forming a capsule out of/from the solution provided in (a), wherein said formation comprises generating an emulsion of at least two phases, said emulsion containing the solution provided in (a) as a first phase and at least one further phase, which is substantially immiscible with said first phase, and forming a polymer network of the polypeptide at the interface of the at least two phases.

In one further (alternatively or additionally) preferred embodiment, the method further comprises the step of:
(c) separating the protein polymer network (capsule) from the emulsion. This can be done by centrifugation, sedimentation, and/or filtration.

A preferred method for producing capsules form the polypeptide is described in WO 2007/014755 A1.

The article may also be a granule or gel. A preferred method for producing gels from the polypeptide is described in WO 2007/014755 A1.

In a sixth aspect, the present invention relates to a pharmaceutical composition comprising the article of the fourth aspect.

The article may also be named antigen carrier or antigen carrier vehicle.

The article may be selected from the group consisting of a particle, capsule, fiber, and film. It is preferred that said article is not cytotoxic and not immunogenic. It is further (alternatively or additionally) preferred that said article is sterilizable.

The inventors of the present patent application surprisingly found that after systemic administration of the articles, article accumulation in the local lymph nodes and/or in antigen presenting cells, in particular in dendritic cells and/or macrophages, occurred. In addition, the articles formed a depot under the skin. The antigen carried by the article induced an immune response in said cells.

Said pharmaceutical composition is useful for treating, preventing, or reducing the severity of a disease or disorder. It may be administered locally or systemically. It is preferred that the pharmaceutical composition is formulated for local administration or systemic administration. In particular, the local administration is by parenteral administration, e.g. by intravenous administration, subcutaneous administration, intradermal administration, intramuscularly administration, and the systemic administration is by intraarterial administration. Preferably the composition is administered subcutaneously, intradermally, or intramuscularly.

It is further preferred that the composition further comprises one or more pharmaceutically acceptable carriers, diluents, and/or excipients. An adjuvant may additionally be present.

The inventors of the present patent application surprisingly found that the use of adjuvants in a pharmaceutical composition comprising antigens which are part of articles, e.g. particles, comprising silk polypeptides is no longer required. The effectiveness of an antigen comprised in a composition without adjuvants is better or at least as good as the same antigen comprised in a composition with adjuvants. The omission of adjuvants has the positive effect that side effects and vaccine incompatibility can be reduced, in some cases even avoided. Thus, it is alternatively preferred that the composition does not further comprise an adjuvant.

In a seventh aspect, the present invention relates to the article of the fourth aspect or the pharmaceutical composition of the sixth aspect for use as a pharmaceutical. The pharmaceutical may be a vaccine, e.g. for inducing an immune response or for immune therapy such as immunization or vaccination, or an anti-cancer medicament.

In an eight aspect, the present invention relates to the article of the fourth aspect or the pharmaceutical composition of the sixth aspect for inducing an immune response.

It is preferred that an immune response against cancer is induced.

The cancer can be, for example, carcinoma, lymphoma, blastoma, sarcoma, or leukemia. More particularly, the cancer can be, for example, bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, or pituitary adenoma.

It is further (alternatively or additionally) preferred that an immune response against an infectious disease or autoimmune disease is induced.

An infectious disease can be, for example, a viral disease, a bacterial disease, or a parasitic disease. More particularly, an infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, or influenza.

An autoimmune disease can be, for example, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, or psoriasis.

The induction of an immune response may result in the immunization or vaccination of the treated subject/patient.

In a ninth aspect, the present invention relates to the article of the fourth aspect or the pharmaceutical composition of the sixth aspect for use in a prophylactic and/or therapeutic treatment of a disease.

It is preferred that the disease is cancer.

The cancer can be, for example, carcinoma, lymphoma, blastoma, sarcoma, or leukemia. More particularly, the cancer can be, for example, bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, or pituitary adenoma.

It is further (alternatively or additionally) preferred that the disease is an infectious disease or an autoimmune disease.

An infectious disease can be, for example, a viral disease, a bacterial disease, or a parasitic disease. More particularly, an infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, or influenza.

An autoimmune disease can be, for example, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, or psoriasis.

It is further preferred that that the disease is a respiratory disease.

The antigen, as described herein, is preferably directly applied to the target area. The direct application of the antigen to the target area allows higher local active pharmaceutical ingredients (API) concentrations while at the same time adverse side effects of a systemic application are minimized. The use of nebulized articles (particles, microparticles or capsules) can improve API deposition in the lower airways. The pulmonary antigen delivery or pulmonary vaccination allows to systemically induce immune response, because a lot of immune cells are located in the mucosa of oral, nasal or pulmonary tissue. The administration of articles (particles, microparticles or capsules) to the lung is an attractive delivery attempt for pulmonary vaccination, because the peptide is protected by the particles and will be released once the particles have been taken up by antigen presenting cells. As there is always a risk to lose loaded antigen during the aerosolization process, the articles of the fourth aspect, the pharmaceutical composition of the sixth aspect, or the articles or pharmaceutical composition used according to the seventh to ninth aspect are a promising alternative. Due to the integration of the active pharmaceutical part into the amino acid sequence of the antigen carrier molecule, the risk of antigen loss during nebulization is very low.

In a further aspect, the present invention relates to the article of the fourth aspect or the pharmaceutical composition of the sixth aspect for stimulating, priming, and/or expanding T cells in a subject.

In a tenth aspect, the present invention relates to a method for delivering an antigen to a cell comprising administering to a subject the article of the fourth aspect or the pharmaceutical composition of the sixth aspect.

In a preferred embodiment, the administering comprises internalization of the article into the cell and releasing the antigen from the article. It is preferred that the antigen is released from the article by an enzyme, which cuts the enzymatically cleavable linker (within the cell, intracellularly), thereby delivering the antigen to the cell. Preferably, the enzymatically cleavable linker is a protease cleavable linker, more preferably a cathepsin cleavable linker, even more preferably a cathepsin S or B cleavable linker, most preferably (i) a cathepsin S cleavable linker having the sequence according to SEQ ID NO: 1 or a variant thereof, or a cathepsin S cleavable linker having the sequence according to SEQ ID NO: 2 or a variant thereof, or (ii) a cathepsin B cleavable linker having the sequence according to SEQ ID NO: 2. The enzyme is preferably a protease, more preferably cathepsin, even more preferably cathepsin S or B.

It is preferred that the cell is an antigen presenting cell. It is more preferred that the antigen presenting cell is a dendritic cell and/or a macrophage.

The subject may be heatlhy and the antigen is delivered for immunization or vaccination. The subject may also be diseased (i.e. a patient), e.g. suffering from cancer, and the antigen is delivered for curing the disease.

In an eleventh aspect, the present invention relates to a method for inducing an immune response in a subject comprising administering to a subject the article of the fourth aspect or the pharmaceutical composition of the sixth aspect.

It is preferred that an immune response against cancer is induced.

The cancer can be, for example, carcinoma, lymphoma, blastoma, sarcoma, or leukemia. More particularly, the cancer can be, for example, bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, or pituitary adenoma.

It is further (alternatively or additionally) preferred that an immune response against an infectious disease or autoimmune disease is induced.

An infectious disease can be, for example, a viral disease, a bacterial disease, or a parasitic disease. More particularly, an infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, or influenza.

An autoimmune disease can be, for example, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, or psoriasis.

The induction of an immune response may result in the immunization or vaccination of the treated subject/patient.

In a twelfth aspect, the present invention relates to a method for prophylactic and/or therapeutic treatment of a disease in a subject comprising administering to a subject the article of the fourth aspect or the pharmaceutical composition of the sixth aspect.

It is preferred that the disease is cancer.

The cancer can be, for example, carcinoma, lymphoma, blastoma, sarcoma, or leukemia. More particularly, the cancer can be, for example, bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, or pituitary adenoma.

It is further (alternatively or additionally) preferred that the disease is an infectious disease or an autoimmune disease.

An infectious disease can be, for example, a viral disease, a bacterial disease, or a parasitic disease. More particularly, an infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, or influenza.

An autoimmune disease can be, for example, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, or psoriasis.

In a thirteenth aspect, the present invention relates to a method for stimulating, priming, and/or expanding T cells in a subject comprising administering to a subject the article of the fourth aspect or the pharmaceutical composition of the sixth aspect.

The present invention is summarized as follows:

1. A polypeptide comprising
   (i) a silk polypeptide and
   (ii) an antigen.
2. The polypeptide of item 1, wherein the polypeptide further comprises an enzymatically cleavable linker.
3. The polypeptide of item 2, wherein the antigen is connected to the silk polypeptide via the enzymatically cleavable linker.
4. The polypeptide of items 2 or 3, wherein the enzymatically cleavable linker is a protease cleavable linker.
5. The polypeptide of item 4, wherein the protease cleavable linker is a cathepsin cleavable linker.
6. The polypeptide of item 5, wherein the cathepsin cleavable linker is a cathepsin S cleavable linker or a cathepsin B cleavable linker.
7. The polypeptide of item 6, wherein
   (i) the cathepsin S cleavable linker has the sequence according to SEQ ID NO: 1 or is a variant thereof, or SEQ ID NO: 2 or is a variant thereof, or
   (ii) the cathepsin B cleavable linker has the sequence according to SEQ ID NO: 2 or is a variant thereof.
8. The polypeptide of any one of items 1 to 7, wherein the silk polypeptide is a recombinant silk polypeptide.
9. The polypeptide of any one of items 1 to 8, wherein the silk polypeptide comprises at least two identical repetitive units.
10. The polypeptide of item 9, wherein the repetitive units are independently selected from the group consisting of module C having the sequence according to SEQ ID NO: 3 or a variant thereof, module $C^{Cys}$ having the sequence according to SEQ ID NO: 4, and module $C^{kappa}$ having the sequence according to SEQ ID NO: 18.
11. The polypeptide of any one of items 1 to 10, wherein the silk polypeptide comprises at least one non-repetitive (NR) unit and/or Tag.
12. The polypeptide of any one of items 1 to 11, wherein the antigen is selected from the group consisting of a viral antigen, a microbial antigen, preferably a bacterial antigen or a fungal antigen, a zooparasitic antigen, and a tumor antigen.
13. A nucleic acid molecule encoding the polypeptide of any one of items 1 to 12.

14. A method for producing a polypeptide comprising the step of:
    (a) expressing the nucleic acid molecule of item 13 in a cell, thereby producing the polypeptide in the cell.
15. The method of item 14, wherein the method further comprises the step of:
    (b) isolating the polypeptide from the cell.
16. An article comprising the polypeptide of any one of items 1 to 12.
17. The article of item 16, wherein the article is selected from the group consisting of a particle, capsule, fiber, film, granule, gel, fabric made of fibers, rod or bundles thereof.
18. The article of item 17, wherein the particle has an average diameter in the range of from 50 nm to 1000 nm.
19. The article of any one of items 17 or 18, wherein the particle has a net negative surface charge.
20. The article of any one of items 17 to 19, wherein the particle is not cytotoxic and not immunogenic.
21. The article of any one of items 17 to 20, wherein the particle is sterilisable.
22. A method for producing an article comprising the steps of:
    (a) providing an aqueous solution comprising the polypeptide of any one of items 1 to 12, and
    (b) forming an article out of/from the solution provided in (a).
23. The method of item 22, wherein the concentration of the polypeptide in the aqueous solution is of between 0.1 wt %/vol and 30 wt %/vol, preferably between 1 wt %/vol and 20 wt %/vol.
24. The method of items 22 or 23, wherein the article is a particle and wherein step (b) comprises triggering aggregation of the polypeptide.
25. The method of item 24, wherein aggregation is triggered by pH shift, ion exchange, shear forces, the addition of alcohol, the addition of a salt, preferably a lyotropic salt, the removal of water, temperature change, and by combinations thereof.
26. The method of item 25, wherein
    (i) the alcohol is ethanol or methanol, or
    (ii) the lyotropic salt is selected from the group consisting of ammonium sulphate, sodium phosphate, and potassium phosphate.
27. The method of any one of items 24 to 26, wherein the method further comprises the step of:
    (c) separating the particle by phase separation.
28. A pharmaceutical composition comprising the article of any one of items 16 to 21.
29. The pharmaceutical composition of item 28, wherein the composition further comprises one or more pharmaceutically acceptable carriers, diluents and/or excipients.
30. The pharmaceutical composition of items 28 or 29, wherein the composition further comprises an adjuvant.
31. The pharmaceutical composition of items 28 or 29, wherein the composition does not further comprise an adjuvant.
32. The article of any one of items 16 to 21 or the pharmaceutical composition of any one of items 28 to 31 for use as a pharmaceutical.
33. The article of any one of items 16 to 21 or the pharmaceutical composition of any one of items 28 to 31 for inducing an immune response.
34. The article of any one of items 16 to 21 or the pharmaceutical composition of any one of items 28 to 31 for use in a prophylactic and/or therapeutic treatment of a disease.
35. A method for delivering an antigen to a cell comprising administering to a subject the article of any one of items 16 to 21 or the pharmaceutical composition of any one of items 28 to 31.
36. The method of item 35, wherein the cell is an antigen presenting cell.
37. The method of item 36, wherein the antigen presenting cell is a dendritic cell and/or a macrophage.
38. A method for inducing an immune response in a subject comprising administering to a subject the article of any one of items 16 to 21 or the pharmaceutical composition of any one of items 28 to 31.
39. A method for prophylactic and/or therapeutic treatment of a disease in a subject comprising administering to a subject the article of any one of items 16 to 21 or the pharmaceutical composition of any one of items 28 to 31.
40. A method for stimulating, priming, and/or expanding T cells in a subject comprising administering to a subject the article of any one of items 16 to 21 or the pharmaceutical composition of any one of items 28 to 31.

The sequence listing comprises the following sequences:

| | |
|---|---|
| SEQ ID NO: 1 | cathepsin S cleavable linker |
| SEQ ID NO: 2 | cathepsin S and B cleavable linker |
| SEQ ID NO: 3 | module C |
| SEQ ID NO: 4 | module $C^{Cys}$ |
| SEQ ID NO: 5 | T7-Tag |
| SEQ ID NO: 6 | T7-Tag |
| SEQ ID NO: 7 | NR3 unit |
| SEQ ID NO: 8 | NR4 unit |
| SEQ ID NO: 9 | NR5 unit |
| SEQ ID NO: 10 | NR6 unit |
| SEQ ID NO: 11 | epitope of chicken-Ovalbumin ($OVA_{257-264}$), SIINFEKL |
| SEQ ID NO: 12 | C16 |
| SEQ ID NO: 13 | C16-SIINFEKL |
| SEQ ID NO: 14 | C16-CathS-SIINFEKL |
| SEQ ID NO: 15 | C16-CathB-SIINFEKL |
| SEQ ID NO: 16 | IGSIINFEKLG sequence cleaved from the hybrid polypeptide comprising the cathepsin B cleavable linker and the epitope of chicken-Ovalbumin ($OVA_{257-264}$) |
| SEQ ID NO: 17 | LPGSIINFEKLG sequence cleaved from the hybrid polypeptide comprising the cathepsin S cleavable linker and the epitope of chicken-Ovalbumin ($OVA_{257-264}$) |
| SEQ ID NO: 18: | module $C^{kappa}$ |

Regarding SEQ ID NO: 12 to SEQ ID NO: 15 it should be noted that the C-terminal G (Gly) may be present or not.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following figures and examples are merely illustrative of the present invention and should not be construed to limit the scope of the invention as indicated by the appended claims in any way.

FIG. 1A shows a dot plot from flow cytometry with propidium iodide (PI) and annexin V. BMDC ($5 \times 10^4$ cells/well) were cultured with spider silk particles at 505 ug particle/mL (=10 ug SIINFEKL (SEQ ID NO: 11)/mL). After 24 hours of incubation, BMDC viability was assessed by flow cytometry and MTT assay.

(FIG. 1A) Representative dot plot from flow cytometry with propidium iodide (PI) and annexin V.

(FIG. 1B) Scheme of the gating strategy to quantify live healthy cells (annexin V−/PI−).

(FIG. 1C) Percentage of live healthy cells (annexin V−/PI−).

(FIG. 1D) Optical density (OD) at 570 nm correlating with formazan production from the MTT assay.

Condition without cells (medium only) was used as control. n.d.: not done. Asterisks (****, $P<0.0001$) indicate significant differences with untreated control group using one-way ANOVA followed by Dunnett's multiple comparison test. (FIG. 1C and FIG. 1D) Each bar represents mean±SEM of 3 independent experiments performed in duplicate. (Except for Panel C, C16-SIIN: tested once in duplicate). Medium only was used as control, untreated: untreated control group; SIIN: SIINFEKL (SEQ ID NO: 11) peptide alone; C16: native C16 particles; C16-SIIN; C16-CathBseq-SIIN, C16-CathSseq-SIIN hybrid protein particles.

FIG. 2A shows the median fluorescent intensity (MFI) of BMDC surface activation markers MHC I and MHC II of BMDC cell cultured with SIIN, CathBseq-SIIN and C16-CathSseq-SIIN compared to untreated sample. FIG. 2B shows the Cytokine quantification with ELISA. R848 (R8), a TLR7 agonist, was used as positive control. BMDC ($5 \times 10^4$ cells/well) were cultured with spider silk particles at 50 ug particle/mL. After 24 hours of incubation, BMDC were analysed by flow cytometry, whereas supernatant was collected for cytokine quantification.

(FIG. 2A) Median fluorescent intensity (MFI) of BMDC surface activation markers: fold change compared to untreated sample.

(FIG. 2B) Cytokine quantification with ELISA. R848 (R8), a TLR7 agonist, was used as positive control (0.25 ug/mL). Asterisks (***, $P<0.001$) indicate significant differences with untreated control group using one-way ANOVA followed by Dunnett's multiple comparison test. Each bar represents mean±SEM of 4 independent experiments performed in duplicate.

FIG. 3A shows the uptake of C16 particles without SIIN (C16), C16 hybrid particles C16-SIIN, C16 hybrid particles with Cathepsin B cleavage site (C16-CathBseq-SIIN) and C16 hybrid particles with Cathepsin S cleavage site (C16-CathSseq-SIIN). Untreated cells (untreated) and SIIN polypeptide (SIIN) serve as controls. FIG. 3B shows the percentage of FITC-positive cells determined in defined immune cell populations: T cells (CD3+), dendritic cells (CD11c+CD11b+) and monocytes/macrophages (CD11c−CD11b+) compared to untreated cells.

(FIG. 3A) BMDC ($5 \times 10^4$ cells/well) were cultured with FITC-labelled spider silk particles at 50 ug particles/mL. After 24 hours of incubation, BMDC were isolated for flow cytometry analysis. Percentage of FITC-positive cells within BMDC (CD11c+) population was determined. Each bar represents mean±SEM of 2 independent experiments performed in duplicate. (Except for C16-SIIN: tested once in duplicate).

(FIG. 3B) Freshly isolated splenocytes ($5 \times 10^4$ cells/well) were cultured 6 hours with FITC-labelled spider silk particles. After 6 hours of incubation, cells were analysed by flow cytometry. Percentage of FITC-positive cells was determined in defined immune cell populations: T cells (CD3+), dendritic cells (CD11c+CD11b+) and monocytes/macrophages (CD11c−CD11b+). Graph depicts one representative experiment of 3. Each experiment was performed in duplicate.

FIG. 4 shows the percentage of proliferating CD8 T-cells within the T cell population (CD3+CD8+). The percentage of proliferating of CD8 T-cells exposed to BMDC cells with C16 CathSseq-SIINFEKL particles and C16 CathBseq-SIINFEKL particles was significantly higher compared to the untreated control. The percentage of proliferating of CD8 T-cells exposed to BMDC cells with C16 CathSseq-SIINFEKL particles was further significantly higher than the percentage of exposed to BMDC cells with C16 CathBseq-SIINFEKL particles. BMDC ($5 \times 10^4$ cells/well) were cultured with spider silk particles at 50 ug particles/mL. R848 (0.25 ug/mL) was used as adjuvant for BMDC activation. After 24 hours of incubation, CFSE labelled CD3+CD8+ OT-I cells ($10^5$ cells/well) were added. After 3 days of co-culture, the cells were analyzed by flow cytometry.

Percentage of proliferating cells within the T cell population (CD3+CD8+). Each bar represents mean±SEM of 2 independent experiments performed in quadruplicate. Asterisks (**, $P<0.01$) indicate significant differences between R848-treated groups using two-way ANOVA followed by Tukey's multiple comparison test.

Figure 5B:
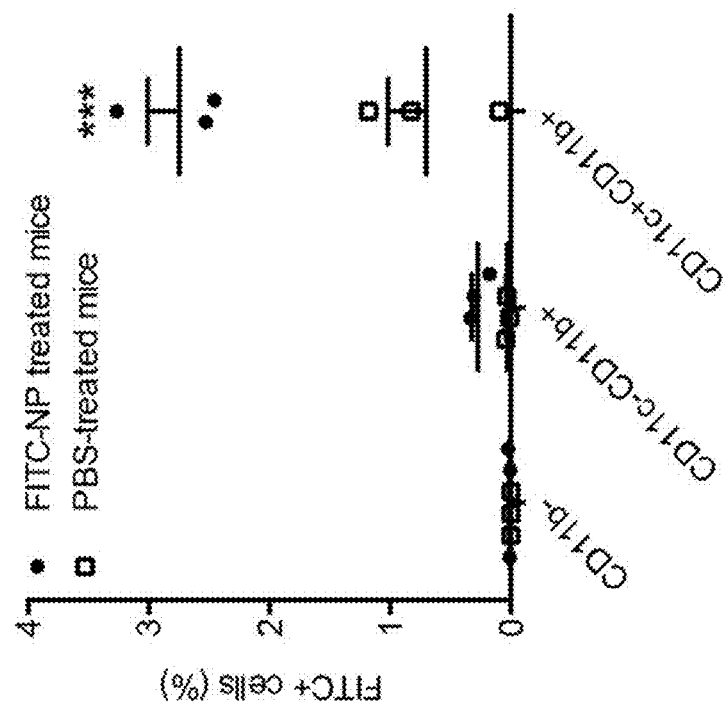
Figure 5A:
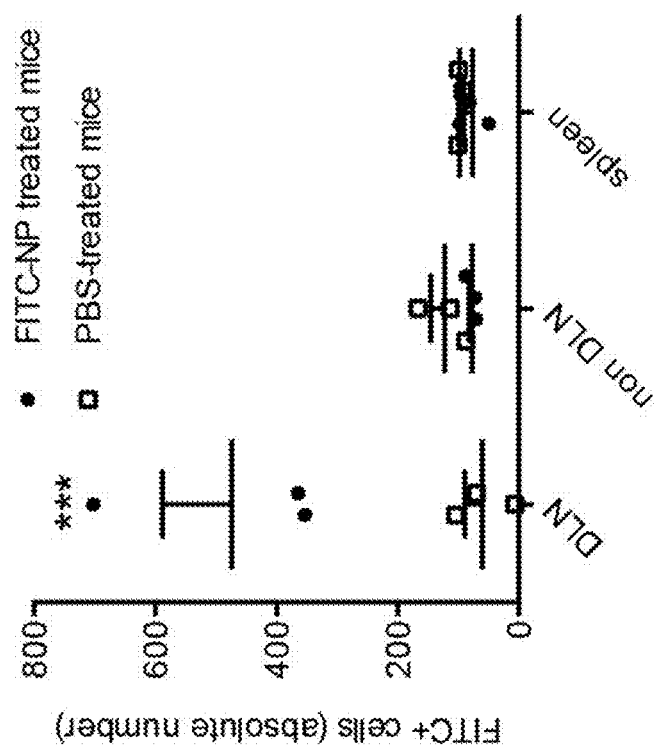

FIGS. 5A-5B: Hybrid Spider Silk Particles Accumulate in the Draining Lymph Node In Vivo.

FIG. 5A shows the number of FITC positive cells (comprising FITC-labelled C16-CathSseq-SIINFEKL particles) in draining lymph nodes (DLN) of 3 FITC-particle treated mice compared to a control group of 3 PBS treated mice in several tissues (DLN, non-DLN and spleen).

FITC-labelled C16-CathSseq-SIINFEKL particles were injected subcutaneously into the right flank of 3 mice (505 ug particles in 100 μL PBS per mouse). PBS was used as negative control. After 24 hours, the ipsilateral draining lymph nodes (DLN), the contralateral lymph nodes (non DLN) and the spleen were isolated for flow cytometry analysis.

(FIG. 5A) Number of FITC-positive cells in the different lymphatic organs (FIG. 5B) Percentage of FITC-positive cells within defined immune cell populations.

Each dot represents one mouse. Bars represent mean±SEM. Asterisks (***, $P<0.001$) indicate significant differences when comparing FITC-particle treated mice with PBS-treated mice using two-way ANOVA followed by Bonferroni's multiple comparison test.

FIG. 5A shows that C16-CathSseq-SIINFEKL particles accumulated in the draining lymph node (DLN) after administration. The results illustrated in FIG. 5B point towards an uptake by dendritic cells (CD11c+CD11b+) rather than by macrophages (CD11c−CD11b+) or leukocytes (CD11b−).

Figure 6:
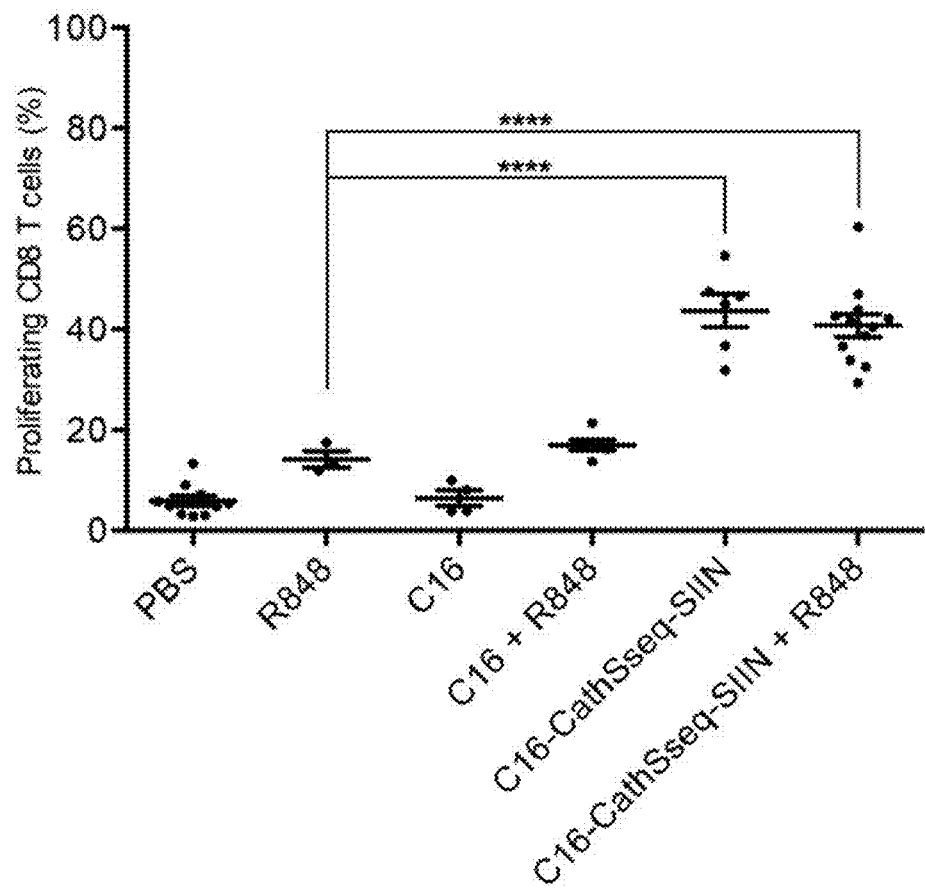

FIG. 6: SIINFEKL (SEQ ID NO: 11)-Containing Spider Silk Particles Induce Antigen-Dependent T-Cell Proliferation In Vivo.

FIG. 6 shows the proliferation of CD8 T cells of mice immunized with C16-CathSseq-SIINFEKL particles. The proliferation of CD8 T cells was significantly higher without R848 adjuvant.

$10^6$ CFSE-labelled CD3+CD8+ OT-I cells in 100 μL of PBS were injected intravenously into mice (each dot represents one mouse). 18 hours later, mice were vaccinated with spider silk particles (505 ug particles in 100 μL PBS per mouse). R848 (25 ug) was used as adjuvant. 3 days after vaccination, the DLN were isolated for flow cytometry analysis to determine the proliferation of CD3+CD8+ CFSE-labelled OT-I cells. Each dot represents one mouse. Bars represent mean±SEM. Asterisks (****, P<0.0001) indicate significant differences with R848-treated control using one-way ANOVA followed by Dunnett's multiple comparison test. The proliferation of CD8 T cells was higher without R848 adjuvant. It could be shown that the C16-CathSseq-SIINFEKL protein particles were able to induce similar to respectively higher level of proliferating CD8+ T cells either with, but also without the use of the immunostimulatory adjuvant R848.

Figure 7A:
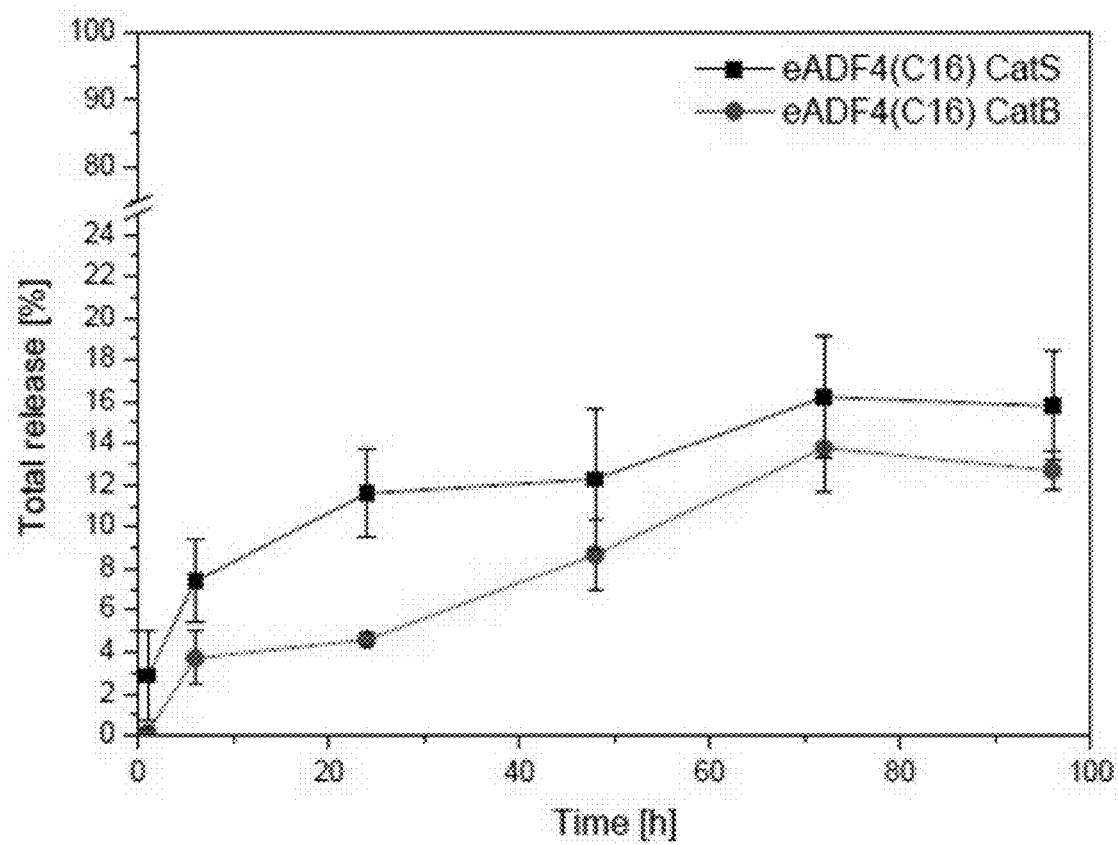
Figure 7B:
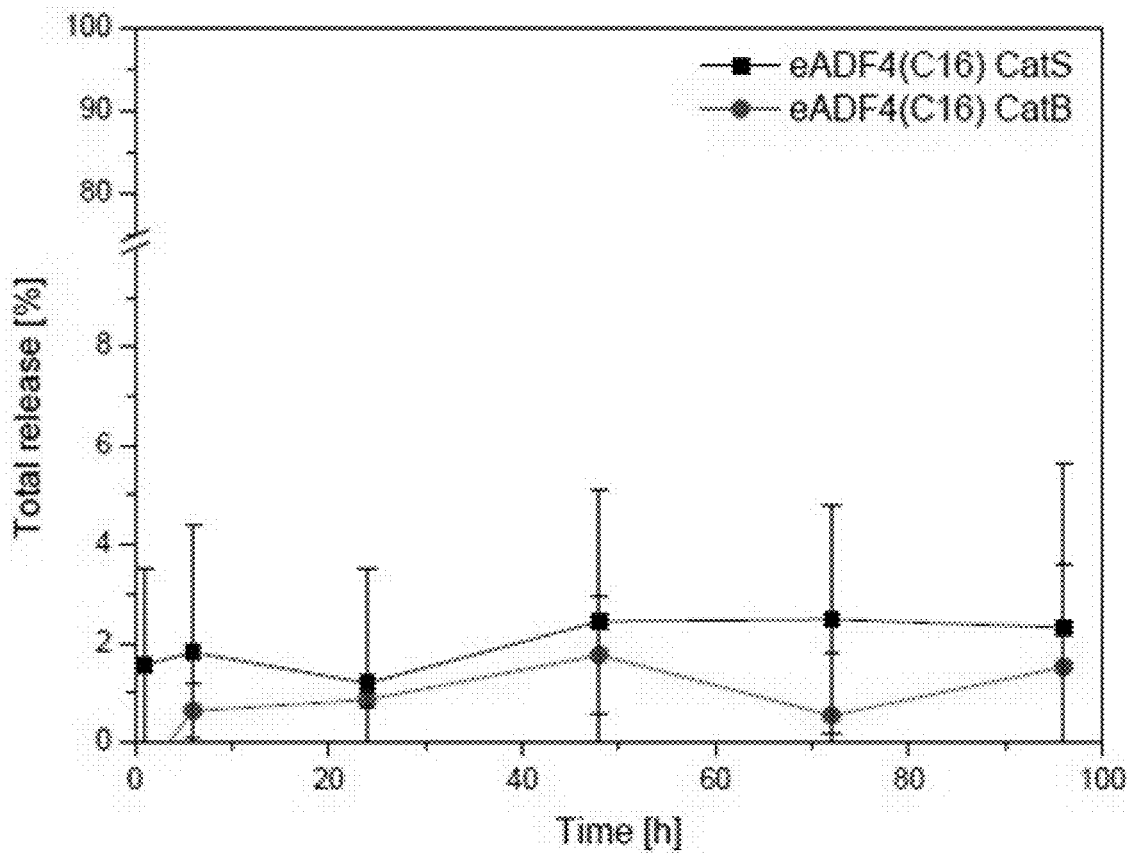

FIGS. 7A-7B: Cathepsin S Enzyme Incubation of C16 Particles C16-CathB-SIINFEKL and C16-CathS-SIINFEKL with Cathepsin S and Cathepsin B Enzymes In Vitro Differential release of the antigen with different cathepsin enzymes. The sequence LPGSIINFEKLG (SEQ ID NO: 17) was released from C16-CathS-SIINFEKL hybrid protein particles, while the sequence IGSIINFEKLG (SEQ ID NO: 16) was released from C16-CathB-SIINFEKL hybrid protein particles. Said sequences comprise the sequence SIINFEKL (SEQ ID NO: 11). Data are the mean and SD (standard deviation) of 3 independent replicates. Cathepsin S enzyme shows the better cleavage of SIINFEKL (SEQ ID NO: 11) peptides from both C16 hybrid protein particles than cathepsin B. Cathepsin S also cleaves SIINFEKL (SEQ ID NO: 11) peptides from particles designed for cathepsin B release.

(FIG. 7A) eADF4(C16) hybrid protein particles incubated with cathepsin S enzyme for 96 hours.

(FIG. 7B) eADF4(C16) hybrid protein particles incubated with cathepsin B enzyme for 96 hours.

EXAMPLES

The examples given below are for illustrative purposes only and do not limit the invention described above in any way.

The terms "NP" and "spider silk particle", the terms "SIIN" and "SIINFEKL", the terms "C16-CathB-SIINFEKL", "C16-CathB-SIIN", "eADF4(C16) CathB" and "SSP25-eADF4(C16-CathB-CD8)", the terms "C16-CathS-SIINFEKL", "C16-CathS-SIIN", "eADF4(C16) CathS" and SSP26-eADF4(C16-CathS-CD8)" as well as the terms "SIIN" and "SIINFEKL" are used interchangeably herein. SIINFEKL (SEQ ID NO: 11) represents the amino acid sequence of an epitope of chicken-Ovalbumin ($OVA_{257-264}$). This antigen stimulates an immune response via interaction with MHC I and CD8 T-cell receptor.

Example 1: Production of Silk Polypeptide Antigen Particles

The polypeptides SSP25-eADF4(C16-CathS-CD8) (1), SSP26-eADF4(C16-CathB-CD8) (2), C16-SIIN (3) and C16 (4) were synthesized via gene syntheses at Geneart (Regensburg).

(1) C16-CathS-SIINFEKL respectively SSP26-eADF4 (C16-CathS-CD8) (SEQ ID NO: 14)
(C16) GPMGLPG SIINFEKL
Hybrid polypeptide comprising C16, a Cathepsin S protease cleavage site, and SIINFEKL (SEQ ID NO: 11).
(2) C16-CathB-SIINFEKL respectively SSP25-eADF4 (C16-CathB-CD8) (SEQ ID NO: 15)
(C16) GAVGFLGIG SIINFEKL
Hybrid polypeptide comprising C16, a Cathepsin B protease cleavage site, and SIINFEKL (SEQ ID NO: 11).
(3) C16-SIINFEKL (SEQ ID NO: 13)
(C16) GGSG SIINFEKL
Hybrid polypeptide comprising C16 and SIINFEKL (SEQ ID NO: 11).
(4) C16 (SEQ ID NO: 12)
C16
Hybrid polypeptide without antigen (SIINFEKL (SEQ ID NO: 11)).

The polypeptides encoding SSP25-eADF4(C16-CathB-CD8), SSP26-eADF4(C16-CathS-CD8), C16-SIINFEKL and C16 were produced and purified as described in WO 2006/008163 A2.

Example 2: Sterilization by Autoclave Treatment

In a first step, about 150 mg of the protein (C16-CathB-SIINFEKL, C16-CathS-SIINFEKL, C16-SIINFEKL and C16) were weighed into glass vials (DIN 10R). The C16 protein was subsequently suspended with 7.5 ml HPW (highly purified water). The vials were closed with rubber stoppers and crimped with aluminum caps. Steam sterilization was performed for 15 minutes at 121° C. in a GTA 50 autoclave (Fritz Gossner, Hamburg, Germany). After cooling down, the C16 protein suspension was centrifuged at 10,000 rpm (SIGMA 4K15, Sigma Laborzentrifugen, Osterode am Harz, Germany) for 30 minutes and the supernatant was discarded. The centrifuged C16 protein was dissolved in a 6 M guanidine thiocyanate solution and dialyzed against an endotoxin free 10 mM TRIS/HCl solution pH 8.0 for 24 h.

The protein concentration of C16-CathB-SIINFEKL after dialysis was 3.91 mg/ml, the protein concentration of C16-CathS-SIINFEKL was 3.56 mg/ml, the protein concentration of C16-SIINFEKL was 3.81 mg/ml and the protein concentration of C16 was 3.88 mg/ml. The protein concentration of all solutions was adjusted to 1 mg/ml. The endotoxin values of the solutions were <0.200 EU/mg. Sterilization of spider silk particles had no detrimental effect on particle size, secondary structure and thermal stability. After sterilization by autoclave treatment, no changes in size or secondary structure of the particles as well as no functional changes were observed. Remaining the function after sterilization is advantageous in view of the systems of the prior art.

Example 3: Particle Preparation

After endotoxin removal, the protein solutions (C16-CathB-SIINFEKL, C16-CathS-SIINFEKL, C16-SIINFEKL and C16) were adjusted to 1 mg/ml with endotoxin free 10 mM TRIS/HCl buffer pH 8.0 for particle preparation. The particle preparation was carried out by micromixing using a high pressure syringe pump system. The syringe pump cylinders were depyrogenized by 70% (v/v) ethanol over 48 h. Subsequently, the cylinders were washed three times with HPW to remove any organic solvent. After depyrogenation, both cylinders of the syringe pump system (Model 100 DX and Series D pump controller, Teledyne Isco, Lincoln, USA) were filled with pre-tempered C16 solution and pre-tempered endotoxin free 2 M potassium phosphate buffer pH 8.0 or 4 M ammonium sulfate solution of 80°. The solutions were pumped at a high flow rate of 50 ml/min to a T-shape mixing element (inner diameter 0.5 mm, P-727 PEEK tee, Upchurch Scientific, Oak Harbor, USA) leading to an outlet tubing (inner diameter 0.5 mm, 1532 PEEK Tubing, Upchurch Scientific, Oak Harbor, USA) for suspension collection. The C16 particle suspensions were subsequently centrifuged at 14,000 rpm (SIGMA 4K15, Sigma Laborzentrifugen, Osterode am Harz, Germany) and washed with HPW three times. A two minute ultrasonication (Sonopuls HD 3200, Bandelin electronic, Berlin, Germany) step completed the particle preparation procedure. The particle concentrations in mg/ml were determined gravimetrically after drying the particles under vacuum (13 mbar) overnight.

The particle concentration of C16-CathB-SIINFEKL was 32.75 mg/ml, the protein concentration of C16-CathS-SIINFEKL was 34.72 mg/ml, the protein concentration of C16-SIINFEKL was 30.06 mg/ml and the protein concentration of C16 was 32.52 mg/ml.

Example 4: Optimizing C16 Particle Size

The micromixing particle preparation process was analyzed for further reduction of the final particle size. Some parameters were selected to be changed compared to the preparation process above. The concentration of the C16 solution used for particle preparation was adjusted to 0.5-1.0 mg/ml. The 2 M potassium phosphate solution used for particle precipitation so far was complemented by a 2 M, a 3 M and a 4 M ammonium sulfate solution. The flow rate of the salt solution was kept at 50 ml/min, whereas the flow rate of the protein solution was set to 25-50 ml/min. For this studies, native C16 protein was used. All other parameters were kept as described above and final particle size was analyzed after particle preparation with the modified syringe pump settings described here. The resulting particles have an average diameter in the range of from 250 nm to 520 nm Example 5: In Vitro Release of SIINFEKL (SEQ ID NO: 11) from Hybrid C16 Particles (In Vitro)

The release of the antigen sequence SIINFEKL (SEQ ID NO: 11) from the hybrid polypeptides SSP25-eADF4(C16-CathB-CD8) and SSP26-eADF4(C16-CathS-CD8) was tested by the addition of cathepsin enzymes. As the hybrid polypeptides contain cleavable linker sequences for the cathepsin S and cathepsin B enzymes, these two cathepsins were also used for the in vitro release studies.

The C16 hybrid polypeptide particles were suspended to a final concentration of 2 mg/ml with a 50 mM sodium acetate buffer, pH 5.5, containing 1 mM EDTA and 2 mM DTT for incubation with the cathepsin S enzyme. Cathepsin S was diluted in the same buffer to a final concentration of 0.9 mU/ml. Slight pH modification of the buffer was realized for the cathepsin B enzyme.

The C16 hybrid polypeptide particles were suspended to a final concentration of 2 mg/ml with a 50 mM sodium acetate buffer, pH 5.0, containing 1 mM EDTA and 2 mM DTT for incubation with the cathepsin B enzyme. Cathepsin B was diluted in the same buffer to a final concentration of 0.1 U/ml. The incubation of the particles with the enzymes was carried out at 37° C. on a waving platform shaker (Heidolph Polymax 1040, Heidolph Instruments GmbH, Schwabach, Germany) at 10 rpm. Samples (supernatant) were drawn after 1, 6, 24, 48, 72 and 96 h and used for analysis by RP-HPLC.

The cleaved SIINFEKL (SEQ ID NO: 11) peptide fragments were analyzed by RP-HPLC. The supernatant of each sample was removed from the particles by centrifugation (two times at 12,000 rpm for 30 minutes). The pellets were discarded and 180 µl of the supernatant was filled into HPLC glass inserts and analyzed by RP-HPLC (detection by UV-Vis at 220 nm). Volumes of 50 µl of the corresponding supernatants were separated at 30° C. by a reversed phase YMC-Triart C18 column (YMC Europe GmbH, Dinslaken, Germany) using a Waters 2695 separations module (Waters Corporation, Milford, MA, USA). A gradient with two mobile phases was applied, using water+0.1% [m/m] TFA (mobile phase A) and 100% acetonitrile+0.1% [m/m] TFA (mobile phase B). Each run started with two minutes of 95% mobile phase A and was followed by a linear increase of mobile phase B from 5% to 100% over 28 minutes. A five minute washing step with 100% mobile phase B was used to wash residual peptide/protein from the column. The separation run stopped with a five minute equilibration of the column at 95% mobile phase A. The detection was carried out on a Waters UV-Vis detector 2487 (Waters Corporation, Milford, MA, USA) at a wavelength of 220 nm to detect the SIINFEKL (SEQ ID NO: 11) peptides. The amount of the released SIINFEKL (SEQ ID NO: 11) peptides was analyzed using a standard curve. In particular, cleaving the SIINFEKL (SEQ ID NO: 11) peptide of the hybrid polypeptide with the cathepsin S cleavable linker resulted in a peptide with the sequence IGSIINFEKLG (SEQ ID NO: 16). In addition, cleaving the SIINFEKL (SEQ ID NO: 11) peptide of the hybrid polypeptide with the cathepsin S cleavable linker resulted in a peptide with the sequence LPGSIINFEKLG (SEQ ID NO: 17). SIINFEKL (SEQ ID NO: 11) is comprised in IGSIINFEKLG (SEQ ID NO: 16) as well as in LPGSIINFEKLG (SEQ ID NO: 17). These two peptides were used for the standard curve at concentrations of 10, 20, 30, 50 and 100 µg/ml dissolved in 50% DMSO/50% water. The area of each of the peptides in the chromatogram was integrated and used for calculation of calibration curves after injection and analysis. Data analysis was performed with Chromeleon® 6.80 software (Dionex GmbH, Germering, Germany).

FIG. 7A shows the total release in percent of the cleaved SIINFEKL (SEQ ID NO: 11) peptides for the hybrid polypeptides SSP25-eADF4(C16-CathB-CD8) and SSP26-eADF4(C16-CathS-CD8) as a function of time (1, 6, 24, 48, 72 and 96 h).

Cathepsin S enzyme shows the better cleavage of SIINFEKL (SEQ ID NO: 11) peptides from both hybrid polypeptide particles. Cathepsin S also cleaves SIINFEKL (SEQ ID NO: 11) peptides from particles designed for cathepsin B release, but slower and in a lesser extent. This could not be expected, because the linker which was assigned for the cleavage by the cathepsin S enzyme (PMGLP, SEQ ID NO: 20) and not for cleavage of the cathepsin B linker sequence (GFLG, SEQ ID NO: 21).

In contrast to Cathepsin B, Cathepsin S is only expressed in certain tissue. Cathepsin S plays a key role in the degradation of antigenic proteins and the further processing via the Major Histocompatibility Complex Class II pathway. Cathepsin S linker particles were chosen for in-vivo mice studies.

FIG. 7 A shows the incubation of the hybrid protein particles with cathepsin S enzyme, while FIG. 7 B shows the incubation of the hybrid protein particles with cathepsin B enzyme. Enzymatic cleavage of the SIINFEKL (SEQ ID NO: 11) peptide from the SSP hybrid protein particles is successful in vitro, which is the basis for the further in vitro and in vivo studies.

Example 6: Spider Silk Hybrid Particles do not Induce BMDC Cytotoxicity

Preparation of Bone Marrow-Derived Dendritic Cells (BMDC)

BMDC were generated from primary bone marrow cells obtained by flushing tibia and femurs of C57BL/6Rj mice with cold PBS. Red blood cells lysis was performed with BD Pharm Lyse (BD Biosciences, USA) for 1 min. Cells were then resuspended in complete BMDC medium consisting of RPMI 1640 (Biowest, France) supplemented with 10% FCS (Biological Industries, Israel), 1% L-glutamine, 50 U/mL Penicillin, 50 U/mL Streptomycin, 50 µM 2-mercaptoethanol and 0.5 mM of sodium pyruvate (all from PAA Laboratories, Austria) supplemented with 40 ng/ml GM-CSF (PeproTech, USA). Loosly adherent cells were harvested after 6 days differentiation. The percentage of CD11c+ CD11b+ cells was routinely over 70%.

Exposure to Spider Silk Particles

BMDC ($5 \times 10^4$ cells per well) were seeded in flat-bottom 96-well plates (Corning, New York, USA) in presence of C16 particles (untreated), C16 hybrid particles (with SIIN polypeptide (SIIN), SEQ ID NO: 13), C16 hybrid particles with Cathepsin B cleavage site (C16-CathBseq-SIIN, SEQ ID NO: 15) and C16 hybrid particles with Cathepsin S cleavage site (C16-CathSseq-SIIN, SEQ ID NO: 14) at 505 ug particle/mL (=10 ug SIINFEKL (SEQ ID NO: 11)/mL) (This is 10 times more than the concentration used in other in vitro experiments) diluted in 100 µL of complete medium per well. The TLR7 agonist R848 (Invitrogen, USA), was used as immunostimulant. After 24 hours of incubation, cells were harvested for flow cytometry analysis, whereas the supernatant was stored for cytokine quantification. BMDC viability was assessed by flow cytometry and MTT assay.

Fluorescent Labelling

The labelling of C16-, C16-SIIN, C16-CathBseq-SIIN- and C16-CathSseq-SIIN-polypeptides with fluorescein isothiocyanate (FITC) was performed based on the published method by Spieß et al. (Spieß et al. 2010) using the terminal amine group of C16. FITC-labeled The SIIN polypeptides were obtained from GenScript Inc., Piscataway Township, NJ, USA. For the preparation of particles used for in vivo studies, the C16 protein powder dry protein suspended in HPW was autoclaved as described before. After steam sterilization, the autoclaved C16 powder was dissolved in a 6 M guanidine thiocyanate solution but this time dialyzed against an endotoxin free 20 mM HEPES solution pH 8.0 at 2-8° C. for 24 h. After dialysis, centrifugation and filtration, the solution was adjusted to a concentration of 2.0 mg/ml with an endotoxin free 20 mM HEPES solution pH 8.0 for coupling in solution. A 20-fold molar excess of FITC (dissolved in DMSO) was added slowly to the C16 solution. After addition of the whole amount of dissolved FITC, the solution was incubated in the dark for three hours at room temperature. After incubation, the FITC coupled C16 protein solution was filtered first with a 0.2 µm PES filter (VWR International, Radnor, USA) and subsequently filtered with a pre-flushed Mustang® E filter. The filtered FITC coupled C16 protein solution was adjusted to a protein concentration of 1 mg/ml for particle preparation by the syringe pump system at 80° C. All other parameters were identical with the previously described particle preparation process. The fluorescent labelling of particles used only for in vitro studies was carried out at the final particles. The C16 particles were suspended at a concentration of 2.5 mg/ml in an endotoxin free 20 mM HEPES buffer pH 8.0. A 20-fold molar excess of FITC (dissolved in DMSO) was added dropwise to the particle suspension. After incubation for 72 h in the dark, the particles were centrifuged and washed with HPW for three times. Additional ultrasonication for 2 minutes finished the FITC labelling process of final C16 polypeptide particles.

Dynamic Light Scattering (DLS)

Particle size and size distribution of submicroparticles were measured in triplicate by dynamic light scattering (DLS) using a Zetasizer Nano ZS (Malvern Instruments, Worcestershire, UK). Particle size is shown as the Z-average value, and the particle size distribution is displayed by the polydispersity index (PDI). Directly before each measurement, samples were diluted to a final concentration of 0.01 mg/ml with HPW. All measurements were conducted at 25° C.

Cytotoxicity

Cytotoxicity was assed by flow cytometry using propidium iodide (PI) and annexin V staining and by assay. For flow cytometry analysis, BMDC were incubated with APC-annexin V diluted 1:100 in annexin V buffer (both from Biolegend, USA) for 30 min at room temperature. 0.2 µL PI (Sigma-Aldrich, USA) diluted 1:2 in PBS was automatically added by the MACS quant analyzer (Miltenyi Biotec, Germany) just before analysis. All flow cytometry data were analyzed using FlowJo version 10.0.8r1. Staurosporine (1 nM) (Sigma-Aldrich, USA) was used as positive control (not shown). For the MTT assay, Vybrant MTT cell proliferation Assay Kit (Molecular Probes, USA) was used according to manufacturer protocol. For this assay, complete BMDC medium without phenol red (Biowest, France) was used.

BMDC Cell Phenotyping

After washing with FACS buffer consisting of PBS (Eurobio, France) supplemented with 2 mM EDTA (Calbiochem, Germany) and 0.5% BSA (PAA laboratories, Austria), the BMDC cells were incubated with anti-mouse CD16/32 to block Fc receptors (Biolegend, USA). After 10 min incubation at 4° C., antibodies for activation markers or their respective isotype controls were added: PB-CD80, PE-CD86, APC-MI-ICI and FITC-CD11b (all from Biolegend, USA). Dead cells were excluded using zombie violet dye (Biolegend, USA). After 30 minute incubation at 4° C., the cells were washed and resuspended in FACS buffer before acquisition.

Figure 1A:
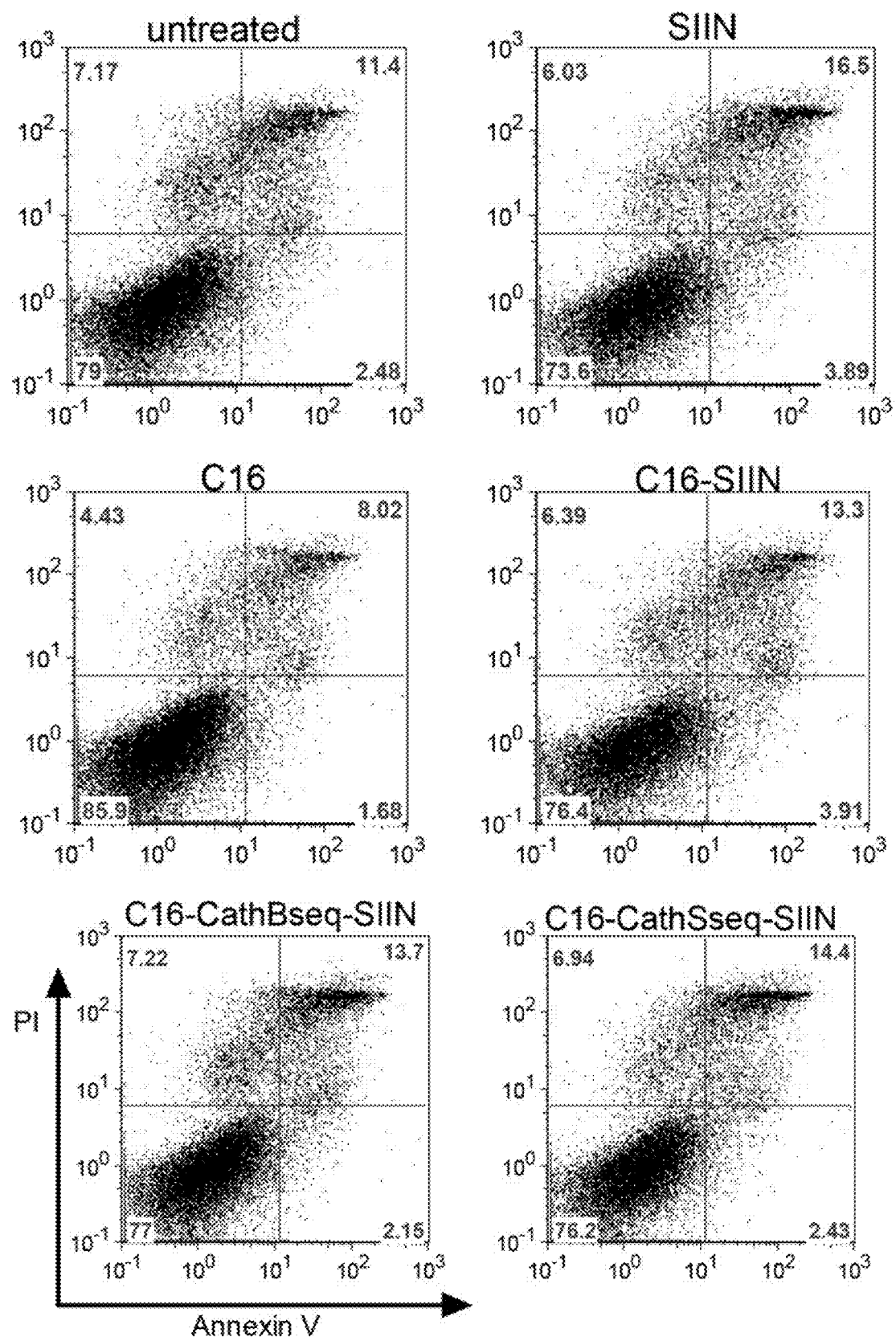
FIGS. 1A-1D: None of the Spider Silk Particles Induce BMDC Cytotoxicity In Vitro

FIG. 1A shows a dot plot from flow cytometry with propidium iodide (PI) and Annexin V. No difference in cell viability could be detected between cells without C16 particles (untreated), SIIN polypeptide (SIIN), C16 particles (C16), C16 hybrid particles with Cathepsin B cleavage site (C16-CathBseq-SIIN) and C16 hybrid particles with Cathepsin S cleavage site (C16-CathSseq-SIIN).

Figure 1B:
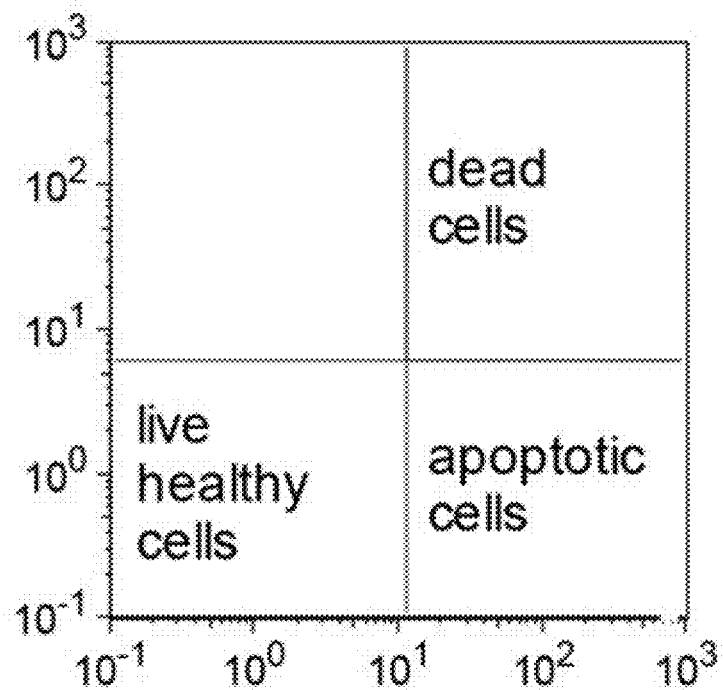

FIG. 1B shows the schematic diagram of live, healthy cells, dead cells and apoptotic cells.

Figure 1C:
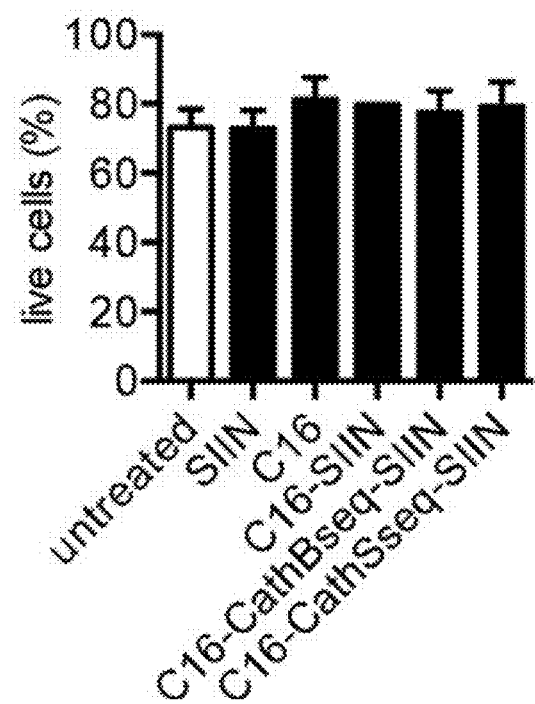

FIG. 1C shows the percentage of live cells with SIIN, C16-CathBseq-SIIN and C16-CathSseq-SIIN compared to untreated cells and cells with C16 particles. No difference in cell viability could be detected between cells without C16 particles (untreated), SIIN polypeptide (SIIN), C16 particles (C16), C16 hybrid particles with Cathepsin B cleavage site (C16-CathBseq-SIIN) and C16 hybrid particles with Cathepsin S cleavage site (C16-CathSseq-SIIN).

Figure 1D:
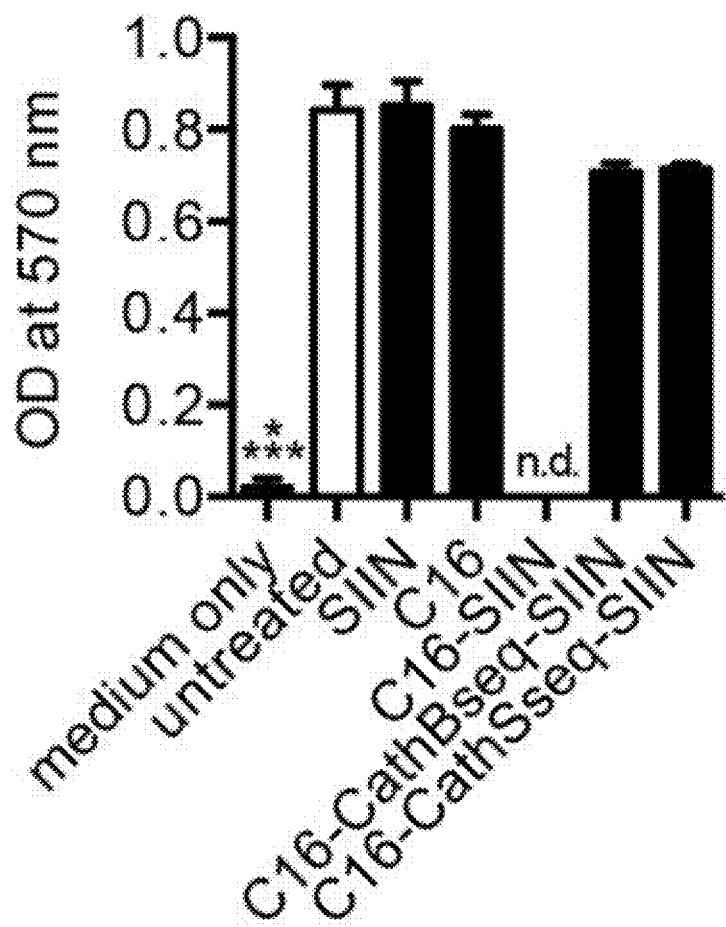

FIG. 1D shows the optical density (OD) at 570 nm correlating with formazan production from the MTT assay.

There is no difference in optical density between spider silk particles as well as the spider silk hybrid particles compared to the control (untreated). This shows that the spider silk particles as well as the spider silk hybrid particles did not induce BDMC cytotoxicity.

Example 7: Spider Silk Particles do not Induce BMDC Immunological Activation In Vitro Preparation of Bone Marrow-Derived Dendritic Cells (BMDC)

BMDC were generated from primary bone marrow cells obtained by flushing tibia and femurs of C57BL/6Rj mice with cold PBS. Red blood cells lysis was performed with BD Pharm Lyse (BD Biosciences, USA) for 1 min. Cells were then resuspended in complete BMDC medium consisting of RPMI 1640 (Biowest, France) supplemented with 10% FCS (Biological Industries, Israel), 1% L-glutamine, 50 U/mL Penicillin, 50 U/mL Streptomycin, 50 µM 2-mercaptoethanol and 0.5 mM of sodium pyruvate (all from PAA Laboratories, Austria) supplemented with 40 ng/ml GM-CSF (PeproTech, USA). Loosly adherent cells were harvested after 6 days differentiation. The percentage of CD11c+CD11b+ cells was routinely over 70%.

The BMDC ($5 \times 10^4$ cells/well) were cultured with spider silk particles at 50 ug particle (spider silk particle)/mL.

BMDC Phenotyping

After washing with FACS buffer consisting of PBS (Eurobio, France) supplemented with 2 mM EDTA (Calbiochem, Germany) and 0.5% BSA (PAA laboratories, Austria), the cells were incubated with anti-mouse CD16/32 to block Fc receptors (Biolegend, USA). After 10 min incubation at 4° C., antibodies for immune activation markers or their respective isotype controls were added: PB-CD80, PE-CD86, APC-MHCI and FITC-CD11b (all from Biolegend, USA). Dead cells were excluded using zombie violet dye (Biolegend, USA). After 30 minute incubation at 4° C., the cells were washed and resuspended in FACS buffer before acquisition.

After 24 hours of incubation, BMDC were analysed by flow cytometry, whereas supernatant was collected for cytokine quantification.

Analysis of Cytokine Production by ELISA

ELISA Max deluxe sets for mouse IL-6 (Biolegend, USA) was used according to the manufacturer's protocol. For protein concentration, absorbance at 570 nm was measured and subtracted from the absorbance at 450 nm by Infinite 200 PRO plate-reader (TECAN, Switzerland). Concentrations were calculated according to the standard curve performed in duplicate.

Figure 2A:
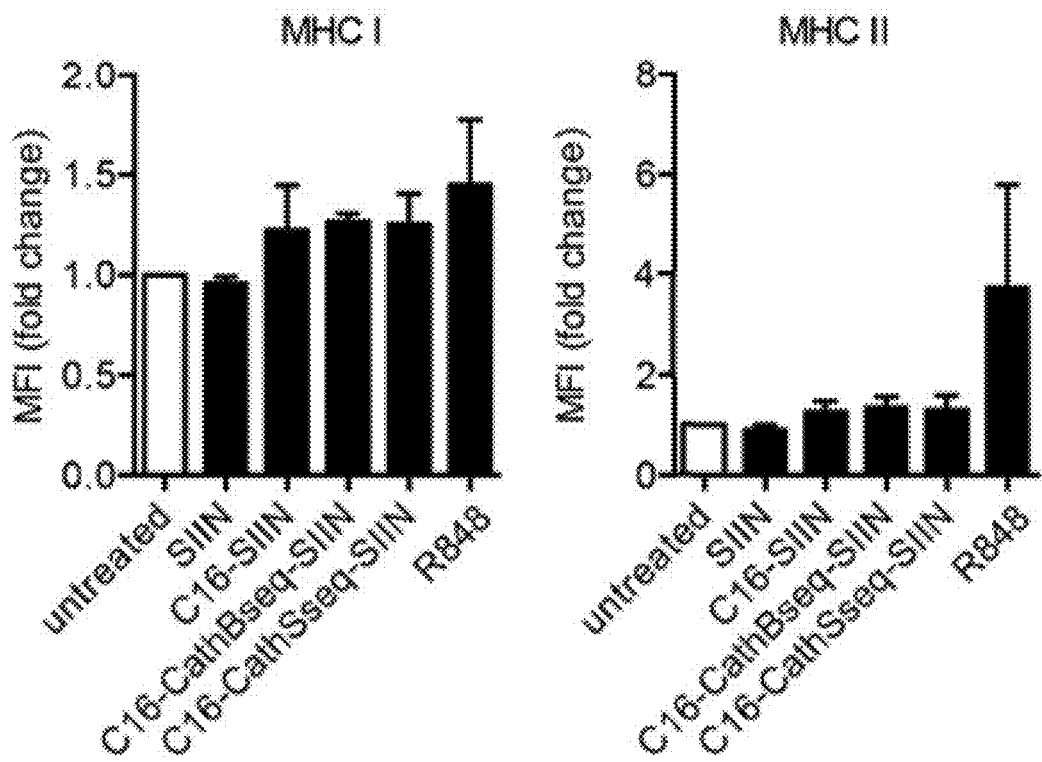
FIGS. 2A-2B: The Spider Silk Particles do not Induce BMDC Immunological Activation In Vitro

FIG. 2A shows the median fluorescent intensity (MFI) of BMDC surface activation markers MHC I and MHC II of BMDC cells cultured with SIIN, C16-SIIN, CathBseq-SIIN and C16-CathSseq-SIIN compared to untreated sample. The adjuvant R848 (R8), a TLR7 agonist, was used as positive control. No significant increase of the immune activation markers MHC I and MHC II could be detected. This shows that the spider silk particles as well as the spider silk hybrid particles are not immunogenic.

Figure 2B:
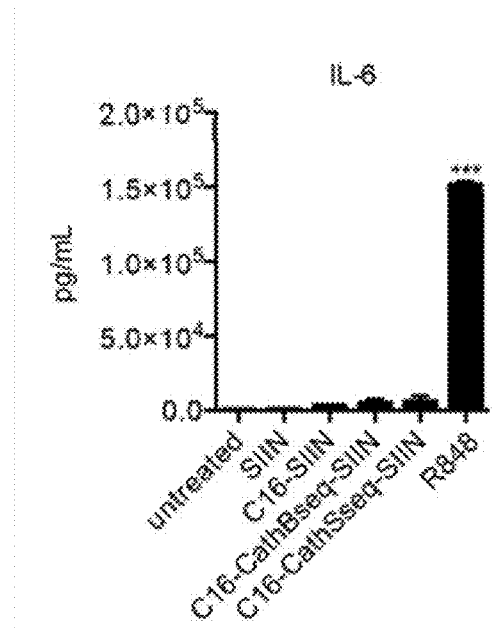

FIG. 2B shows the Cytokine quantification with ELISA. The adjuvant R848 (R8), a TLR7 agonist, was used as positive control. This shows that the spider silk particles as well as the spider silk hybrid particles do not have an intrinsic immunostimulatory activity.

Example 8: Spider Silk Particles are Efficiently Taken Up by Antigen-Presenting Cells BMDC ($5 \times 10^4$ cells/well) were cultured with FITC-labelled spider silk particles (C16-SIIN, C16-CathBseq-SIIN and C16-CathSseq-SIIN) at 50 ug particle/mL according to example 6. After 24 hours of incubation, BMDC were isolated for flow cytometry analysis.

The uptake of spider silk particles by BMDC was assessed by flow cytometry and confocal microscopy. For flow cytometry, dead cells were excluded using zombie violet dye (Biolegend, USA). After Fc receptor blocking, the following antibodies were added: APC-CD11b, APC-Cy7-CD11c (both from Biolegend, USA). Percentage of FITC+ positive cells in the CD11b+CD11c+ population was then determined. For confocal microscopy, BMDC were incubated with Blue DND-22 Lysotracker (Molecular Probes, USA) for 1 hour and FITC-positive particles for an additional 4 hours before imaging with confocal Microscopy (Zeiss, Germany). The percentage of FITC-positive cells within BMDC (CD11c+) population was determined. SIIN polypeptide served as a negative control.

Figures 3A, 3B:
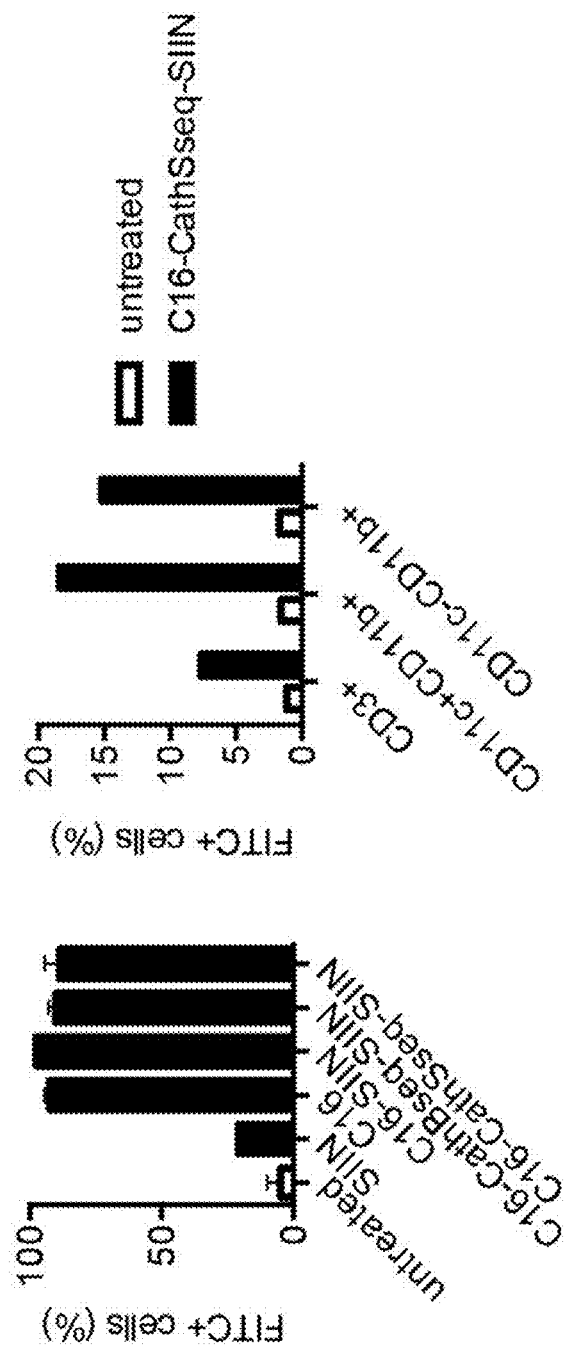
FIGS. 3A-3B: Spider Silk Particles are Efficiently taken up by Antigen-Presenting Cells

FIG. 3A shows the uptake of C16 particles without SIIN (C16), C16 hybrid particles C16-SIIN, C16 hybrid particles with Cathepsin B cleavage site (C16-CathBseq-SIIN) and C16 hybrid particles with Cathepsin S cleavage site (C16-CathSseq-SIIN). Untreated cells (untreated) and SIIN polypeptide (SIIN) served as controls. A particle uptake of more than 90% could be obtained for the hybrid particles. No significant difference in uptake between the hybrid polypeptides C16-CathBseq-SIIN and C16-CathSseq-SIIN and particles without antigen (C16) could be detected. This shows that the hybrid particles are taken up as well as particles without antigen (C16).

Splenocytes were isolated from C57BL/6JRj mice, passed through a 20 µm cell strainer and erythrocyte lysis was performed. Dead cells were excluded using violet zombie dye (Biolegend, USA). The freshly isolated splenocytes ($5 \times 10^4$ cells/well) were cultured 6 hours with FITC-labelled spider silk particles. After Fc receptor blocking, the following antibodies were added: PerCP-CD3, APC-CD11b, APC-Cy7-CD11c (all from Biolegend, USA). After 6 hours of incubation, cells were analysed by flow cytometry.

FIG. 3B shows the percentage of FITC-positive cells determined in defined immune cell populations: T cells (CD3+), dendritic cells (CD11c+CD11b+) and monocytes/macrophages (CD11c−CD11b+) compared to untreated cells. The hybrid particles C16-CathSseq-SIIN were efficiently taken up by dendritic cells, followed by monocytes/macrophages and T cells.

Example 9: Cathepsin S Sequence is More Effective to Induce SIINFEKL (SEQ ID NO: 11) Dependent In Vitro T-Cell Proliferation In Vitro T Cell Proliferation BMDC ($5 \times 10^4$ cells/well) were cultured with spider silk particles at 50 ug particle/mL. R848 (0.25 ug/mL) was used as adjuvant to induce BMDC activation. After 24 hours of incubation, CFSE labelled CD3+CD8+ OT-I cells (105 cells/well) were added. After 3 days of co-culture, the detection of CFSE positive CD3+CD8+ cells were analysed by flow cytometry.

After 24 h incubation, CD8+ T cells were negatively selected from OT-I splenocytes using CD8+ T cell isolation kit (Miltenyi Biotech, Germany). These cells were then stained with CFSE (Molecular Probes, USA) according to manufacturer's protocol and added to the BMDC culture ($10^5$ cells/well). 3 days later, cells were stained for flow cytometry analysis. After Fc blocking, the following antibodies were added: PB-CD3, APC-Cy7-CD8 (all from Biolegend, USA). The proliferation was determined by the percentage of CFSE$^{DIM}$ cells within the CD3+CD8+ cell population.

Figure 4:
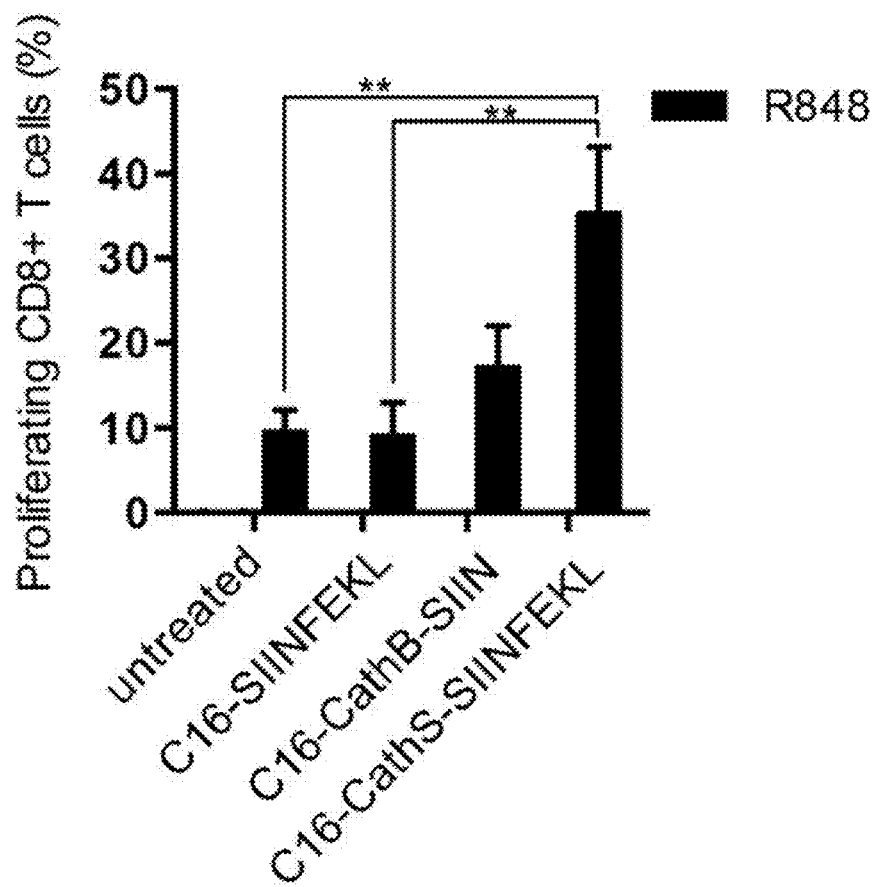
FIG. 4: The Cathepsin S Sequence is the most Effective to Induce SIINFEKL (SEQ ID NO: 11) Dependent In Vitro T-Cell Proliferation

FIG. 4A shows the percentage of proliferating CD8+ T-cells within the T cell population (CD3+CD8+). The percentage of proliferating of CD8 T-cells exposed to BMDC cells with C16 CathSseq-SIINFEKL particles and C16 CathBseq-SIINFEKL particles was significantly higher compared to the untreated control. The percentage of proliferation of CD8 T-cells exposed to BMDC cells with CathSseq-SIINFEKL was further significantly higher than the percentage of CD8 T-cells exposed to BMDC cells with C16 CathBseq-SIINFEKL.

Hybrid protein particles are able to induce a T cell proliferation by the release of the SIINFEKL (SEQ ID NO: 11) peptide. C16-CatS_SIIN particles are more effective than the C16-CatB-SIIN particles.

Example 10: Hybrid Spider Silk Particles Accumulate in the Draining Lymph Node In Vivo For in vivo biodistribution studies, particles were injected in the flank of mice and 24 h later, the mice were sacrificed and organs were harvested for analysis.

Female C57BL/6JRj (Janvier, France) and OVA-TCR transgenic OT-I mice (Charles River, Germany) were housed under specific pathogen-free conditions and used at 6-12 weeks of age. Animal experimentation was conducted according to the Swiss federal law for animal experimentation.

C57BL/6JRj mice were injected subcutaneously with 505 µg FITC-labelled C16-CathSseq-SIINFEKL particles in 100 µL PBS per mouse in the right flank of 3 mice. PBS was used as negative control. After 24 hours, the ipsilateral inguinal draining lymph nodes (DLN), the contralateral inguinal (non-DLN) and the spleen were isolated for flow cytometry analysis and single cell suspensions were made as described above. Dead cells were excluded using violet zombie dye (Biolegend, USA). After Fc receptor blocking, the following antibodies were added: PerCP-CD3, Pe-Cy7-CD11b, APC-CD11c (all from Biolegend, USA).

FIG. 5A shows the number of FITC positive cells (comprising FITC-labelled C16-CathSseq-SIINFEKL particles) in draining lymph nodes (DLN) of 3 FITC-particle treated mice compared to a control group of 3 PBS treated mice in several tissues (DLN, non-DLN and spleen).

The analysis showed that Cathepsin S linker particles (C16-CathSseq-SIINFEKL) accumulated in the local lymph nodes and preferentially in dendritic cells and not in non DLN cells or spleen. During surgery for organ harvesting, particles were still at the place of injection. The C16 hybrid particles are forming a depot under the skin and preferentially accumulate in the local lymph nodes.

FIG. 5B shows the uptake of Cathepsin S linker particles (C16-CathSseq-SIINFEKL) only in dendritic cells (CD11c+ CD11b+) in contrast to monocytes/macrophages (CD11c– CD11b+). Dendritic cells are the most potent class of antigen presenting cells. If presentation of antigen happens at the local lymph nodes, particles do not diffuse uncontrollable through the body.

Example 11: SIINFEKL-Containing Spider Silk Particles Induce Antigen-Dependent T-Cell Proliferation In Vivo In Vivo T-Cell Proliferation After CD8+ T-cell isolation from OT-I splenocytes, the cells were then stained with CFSE according to the manufacturer's protocol in the absence of FCS. $10^6$ CFSE-labelled CD3+CD8+ OT-I cells in 100 µL of PBS were injected intravenously into mice. 18 hours later, mice we in the right flank particles (in 100 µL of PBS) mice were immunized subcuteously with 505 µg C16 and C16-CathSseq-SIINFEKL particles (505 µg particle in 100 µL PBS per mouse). R848 (25 ug in 100 µL) was used as adjuvant. PBS and R848 adjuvant without hybrid particles served as as negative control. 3 days after vaccination, the inguinal DLN were isolated for flow cytometry analysis to determine the proliferation of CD3+CD8+ CFSE-labelled OT-I cells. Single cell suspensions were obtained by passing through a 20 µm cell strainer. After Fc receptor blocking, the following antibodies were added: PB-CD3, APC-Cy7-CD8 (all from Biolegend, USA). The proliferation was determined by the percentage of CFSE$^{DIM}$ cells within the CD3+CD8+ cell population.

Statistical Analysis

All graphs were made with GraphPad prism software version 6.0 g (GraphPad Software, San Diego, USA), where error bars indicate standard error of means (SEM). Statistical significance of multiple groups to control group (untreated sample) was performed using one-way ANOVA followed by Dunnett's multiple comparison test.

FIG. 6 shows the proliferation of CD8 T cells of mice immunized with C16-CathSseq-SIINFEKL particles. The proliferation of CD8 T cells was remarkably higher without R848 adjuvant. It could be shown that the immunization with C16-CathSseq-SIINFEKL without adjuvant resulted in a similar respectively higher proliferation of CD8 T-cells than the immunization with C16-CathSseq-SIINFEKL with adjuvant. This could not be expected, because the immune response is usually higher after the co-administration of an immunostimulatory adjuvant.

The invention claimed is:

1. A method for delivering an antigen to a cell comprising the steps of:
   (i) providing a polypeptide comprising
      (a) a silk polypeptide,
      (b) an antigen, and
      (c) an enzymatically cleavable linker,
      wherein the antigen is connected to the silk polypeptide via the enzymatically cleavable linker, and
   (ii) administering the polypeptide provided in (i) to the cell.

2. The method of claim 1, wherein the cell is a cell of/comprised in a subject.

3. The method of claim 1, wherein the enzymatically cleavable linker is a protease cleavable linker.

4. The method of claim 3, wherein the protease cleavable linker is a cathepsin cleavable linker.

5. The method of claim 4, wherein the cathepsin cleavable linker is a cathepsin S cleavable linker or a cathepsin B cleavable linker.

6. The method of claim 1, wherein the polypeptide is comprised in a pharmaceutical composition which is free of any adjuvant.

7. The method of claim 1, wherein the polypeptide is comprised in an article.

8. The method of claim 7, wherein the article is selected from the group consisting of a particle, capsule, fiber, film, granule, gel, fabric made of fibers, and a rod or bundles thereof.

9. The method of claim 1, wherein the cell is an antigen presenting cell.

10. The method of claim 9, wherein the antigen presenting cell is a dendritic cell and/or a macrophage.

11. A method for prophylactic or therapeutic treatment of a disease in a subject comprising the steps of:
   (i) providing a polypeptide comprising
      (a) a silk polypeptide,
      (b) an antigen, and
      (c) an enzymatically cleavable linker,
      wherein the antigen is connected to the silk polypeptide via the enzymatically cleavable linker, and
   (ii) administering the polypeptide provided in (i) to a subject in need thereof.

12. The method of claim 11, wherein the enzymatically cleavable linker is a protease cleavable linker.

13. The method of claim 12, wherein the protease cleavable linker is a cathepsin cleavable linker.

14. The method of claim 13, wherein the cathepsin cleavable linker is a cathepsin S cleavable linker or a cathepsin B cleavable linker.

15. The method of claim 11, wherein the polypeptide is comprised in an article.

16. The method of claim 15, wherein the article is selected from the group consisting of a particle, capsule, fiber, film, granule, gel, fabric made of fibers, and a rod or bundles thereof.

17. The method of claim 11, wherein the disease is selected from the group consisting of cancer, an infectious disease, and an autoimmune disease.

* * * * *